(12) United States Patent
Eskandarian et al.

(10) Patent No.: US 8,519,853 B2
(45) Date of Patent: Aug. 27, 2013

(54) UNOBTRUSIVE DRIVER DROWSINESS DETECTION SYSTEM AND METHOD

(75) Inventors: Azim Eskandarian, Great Falls, VA (US); Ali Mortazavi, Walnut Creek, CA (US)

(73) Assignee: The George Washington University, Washington, DC (US)

( * ) Notice: Subject to any disclaimer, the term of this patent is extended or adjusted under 35 U.S.C. 154(b) by 800 days.

(21) Appl. No.: 12/613,306

(22) Filed: Nov. 5, 2009

(65) Prior Publication Data

US 2010/0109881 A1    May 6, 2010

Related U.S. Application Data

(60) Provisional application No. 61/193,199, filed on Nov. 5, 2008.

(51) Int. Cl.
*G08B 23/00* (2006.01)
*B60K 28/00* (2006.01)

(52) U.S. Cl.
USPC ............................. 340/575; 180/272

(58) Field of Classification Search
USPC ............... 340/575–579, 425.5, 439; 702/39; 180/272; 701/41
See application file for complete search history.

(56) References Cited

U.S. PATENT DOCUMENTS

| | | | | |
|---|---|---|---|---|
| 4,509,040 A | * | 4/1985 | Seko et al. | 340/576 |
| 4,581,607 A | * | 4/1986 | Seko et al. | 340/576 |
| 4,594,583 A | * | 6/1986 | Seko et al. | 340/576 |
| 4,794,536 A | * | 12/1988 | Eto et al. | 701/41 |
| 5,465,079 A | * | 11/1995 | Bouchard et al. | 340/576 |
| 5,798,695 A | | 8/1998 | Metalis et al. | |
| 5,900,819 A | | 5/1999 | Kyrtsos | |
| 6,822,573 B2 | | 11/2004 | Basir et al. | |
| 2003/0033094 A1 | * | 2/2003 | Huang | 702/39 |
| 2005/0099279 A1 | * | 5/2005 | Forbes et al. | 340/435 |
| 2007/0013498 A1 | * | 1/2007 | Knoll et al. | 340/438 |
| 2007/0080816 A1 | * | 4/2007 | Haque et al. | 340/576 |
| 2010/0019880 A1 | * | 1/2010 | Huang et al. | 340/5.1 |
| 2010/0039249 A1 | * | 2/2010 | Schmitz et al. | 340/439 |

OTHER PUBLICATIONS

N. E. Huang, Z. Shen, S. R. Long, M. C. Wu, H. H. Shih, Q. Zheng, N.C. Yen, C. C. Tung, and H. H. Liu, The empirical mode decomposition and the Hilbert spectrum for nonlinear and non-stationary time series analysis, The Royal Society, received Jun. 3, 1996, accepted Nov. 4, 1996, Proc. R. Soc. Lond. A (1998) 454, pp. 903-995, Great Britain.

(Continued)

*Primary Examiner* — Benjamin C Lee
*Assistant Examiner* — Sigmund Tang
(74) *Attorney, Agent, or Firm* — Blank Rome LLP

(57) ABSTRACT

A drowsiness detection system and method uses Empirical Mode Decomposition (EMD) signal processing to detect whether a vehicle driver is drowsy. The system uses a decomposed component of the steering wheel signal to extract specific features representing the steering control degradation phases. The system classifies the measured features into alert or drowsy state. The detection system is independent of the road geometry and automatically compensates steering control performance variability between drivers. The system is accurate in detecting the drowsy periods and drowsy-related lane departures. The detection system is unobtrusive and can be applied on-line.

23 Claims, 21 Drawing Sheets

(56) References Cited

OTHER PUBLICATIONS

T.M. Mast, H.V. Jones, and N.W. Heimstra, The Effects of Fatigue on Performance in a Simulated Driving Device, Department of Psychology, University of South Dakota, Final Report, Jun. 1964, 31 pgs., Prepared for: South Dakota Department of Highways and U.S. Department of Commerce.
E. I. Dureman and C. Boden, Fatigue in Simulated Car Driving, Ergonomics, 1972, vol. 15, No. 3, pp. 299-308.
J. H. Skipper, An Investigation of Low-Level Stimulus-Induced Measures of Driver Drowsiness, Mar. 15, 1984, pp. 1-291.
T. A. Dingus, H. L. Hardee, and W. W. Wierwille, Development of Models for On-Board Detection of Driver Impairment, Received Feb. 7, 1986, revised Jun. 25, 1986, Accid. Anal. & Prev. vol. 19, No. 4, pp. 271-283, 1987, Pergamon Journals Ltd., Printed in Great Britain.
K. Yabuta, H. Iiizuka T. Yanagishima, Y. Kataoka, and T. Seno, The Development of Drowsiness Warning Devices, Tenth International Technical Conference on Experimental Safety Vehicles, 1986, pp. 282-288.
T. Akerstedt and M. Gillberg, Subjective and Objective Sleepiness in the Active Individual, Received Oct. 16, 1989, revised Dec. 11, 1989, Intern. J. Neuroscience, 1990, vol. 52, pp. 29-37, 1990 Gordon and Breach, Science Publishers, Inc., Printed in the United Kingdom.
C. Petit, D. Chaput, C. Tarriere, J.Y. Le Coz, S. Planque, Research to Prevent the Driver from Falling Asleep Behind the Wheel, 34th Annual Proceedings Association for the Advancement of Automotive Medicine, Oct. 1-3, 1990, Scottsdale, Arizona, pp. 505-522.
R. R. Mackie and C. D. Wylie, Countermeasures to Loss of Alertness in Motor Vehicle Drivers: A Taxonomy and Evaluation, Proceedings of the Human Factors Society 35th Annual Meeting, Sep. 2-6, 1991, vol. 2, pp. 1149-1153.
M. Elling and P. Sherman, Evaluation of Steering Wheel Measures for Drowsy Drivers, Iowa State University, 94AT002, 1994, pp. 207-214.
R. R. Knipling and J.S. Wang, Crashes and Fatalities Related to Driver Drowsiness/Fatigue, Research Note, Nov. 1994, pp. 1-8.
R. R. Knipling and W. W. Wierwille, Vehicle-Based Drowsy Driver Detection: Current Status and Future Prospects, Paper Delivered at the IVHS America Fourth Annual Meeting, Atlanta, GA, Apr. 17-20, 1994, pp. 2-20.
H. Ueno, M. M Kaneda, and M. Tsukino, Development of Drowsiness Detection System, 1994 Vehicle Navigation & Information Systems Conference Proceedings, pp. 15-20.
J. Fukuda, E. Akutsu and K. Aoki, An estimation of driver's drowsiness level using interval of steering adjustment for lane keeping, Technical Notes, JSAE Review 16, 1995, Society of Automotive Engineers of Japan, Inc. and Elsevier Science B.V., Received Sep. 21, 1994, pp. 197-199.
R. S. Huang, C. J. Kuo, L. L. Tsait and O.T.C. Chen, EEG Pattern Recognition—Arousal States Detection and Classification, IEEE, 1996, pp. 641-646.
G. P. Siegmund, D. J. King and D. K. Mumford, Correlation of Steering Behavior with Heavy-Truck Driver Fatigue, Society of Automotive Engineers, Inc., 1996, pp. 17-38.
K. Ogawa and M. Shimotani, A Drowsiness Detection System, Mitsubishi Electric Advance, Technical Reports, vol. 78, Mar. 1997, pp. 13-16.
T. Pilutti and A. G. Ulsoy, Identification of Driver State for Lane-Keeping Tasks: Experimental Results, Proceedings of the American Control Conference, Albuquerque, New Mexico, Jun. 1997, pp. 3370-3374.
T. Pilutti, and A. G. Ulsoy, Identification of Driver State for Lane-Keeping Tasks, IEEE Transactions on Systems, Man, and Cybernetics—Part A: Systems and Humans, vol. 29, No. 5, Sep. 1999, pp. 486-502.
K. Brookhuis, D. de Waard, B. Peters and E. Bekiaris, Save-System for Detection of Driver Impairment and Emergency Handling, Journal of International Association of Traffic and Safety Sciences, IATSS Research, vol. 22, No. 2, Received Jun. 8, 1998, pp. 37-42.
P. Gander and I. James, Investigating Fatigue in Truck Crashes: A New Approach, 1998, 6 pgs.
R. Grace, V. E. Byrne, D. M. Bierman, J. M. Lagrand, D. Gricourt, R. K. Davis, J. J. Staszewski and B. Carnahan, A Drowsy Driver Detection System for Heavy Vehicles, IEEE, copyright 1998, pp. 136-1-136-8.
J. M. Lyznicki, T. C. Doege, R. M. Davis and M. A. Williams, Sleepiness, Driving, and Motor Vehicle Crashes, JAMA, Jun. 17, 1998, vol. 279, No. 23, www.jama.com, pp. 1908-1913.
L. Hartley, T. Horberry, N. Mabbott and G. P. Krueger, Review of Fatigue Detection and Prediction Technologies, Sep. 2000, National Road Transport Commission, www.nrtc.gov.au, pp. 1-31.
A. T. McCartt, J. W. Rohrbaugh, M. C. Hammer and S. Z. Fuller, Factors associated with falling asleep at the wheel among long-distance truck drivers, Accident Analysis and Prevention 32, 2000, Elsevier Science Ltd., www.elsevier.com.locate/aap, pp. 493-504.
R. Sayed and A. Eskandarian, Unobtrusive drowsiness detection by neural network learning of driver steering, Received Jan. 26, 2001, published Jun. 20, 2001, Proc Instn Mech Engrs., vol. 215, Part D, IMechE 2001, pp. 969-975.
R. Sayed and A. Eskandarian, Monitoring Drowsy Drivers with Artificial Neural Network, ITS America Conference, Miami, FL, Jun. 4-8, 2001, 12 pgs.
R. Sayed and A. Eskandarian, Driver Drowsiness Detection Using Artificial Neural Networks, 80th Transportation Research Board Annual Meeting, Committee on Simulation and Measurement of Vehicle and Operator Performance, Washington, DC, Jan. 2001, pp. 1-13.
R. A. Sayed, A. Eskandarian and P. Delaigue, Driver Fatigue: Causes and Countermeasures, International Truck & Bus Safety and Security Symposium, Nov. 14-16, 2005, Alexandria, VA, pp. 100-111.
A. Kircher, M. Uddman and J. Sandin, Vehicle Control and Drowsiness, VTI Meddelande 922A, Swedish National Road and Transport Research Institute, Linkoping Sweden, 2002, 88 pgs.
A. Eskandarian and A. Mortazavi, Evaluation of a Smart Algorithm for Commercial Vehicle Driver Drowsiness Detection, IEEE Intelligent Vehicles Symposium, Jun. 13-15, 2007, Istanbul, Turkey, 7 pgs.
A. Mortazavi, A. Eskandarian and R. A. Sayed, Effect of Drowsiness on Driving Performance Variables of Commercial Vehicle Drivers, Received Mar. 14, 2008, revised Oct. 25, 2008, International Journal of Automotive Technology, vol. 10, No. 0, pp. 1-14.
N. E. Huang, M. L. Wu, W. Qu, S. R. Long, and S. S. P. Shen, Applications of Hilbert-Huang transform to non-stationary financial time series analysis, Applied Stochastic Models in Business and Industry, 2003, accepted Jul. 1, 2003, vol. 19, pp. 245-268, John Wiley & Sons, Ltd.
P. Flandrin and P. Goncalves, Empirical Mode Decompositions as Data-Driven Wavelet-Like Expansions, International Journal of Wavelets, Multiresolution and Information Processing, vol. 2, No. 4, 2004, pp. 477-496, World Scientific, www.worldscientific.com.
G. Rilling, P. Flandrin and P. Goncalves, On Empirical Mode Decomposition and its Algorithms, 5 pgs.

\* cited by examiner

| Subject No | Total No of Detections | Total No of Intervals in which $SEVD>0$ | No of 11,000m Window With No Detection | Average No of Detections | Average No of Intervals in which $SEVD>0$ | Percentage of Time the system was able to detect drowsiness |
|---|---|---|---|---|---|---|
| | | | New Algorithm (1+4x2750m Window)* | | | |
| 1 | 9 | 13 | 0 | 3 | 4.3 | 69% |
| 2 | 89 | 210 | 5 | 2.1 | 5 | 42% |
| 3 | 46 | 58 | 0 | 3.8 | 4.8 | 79% |
| 4 | 89 | 135 | 0 | 3.2 | 5 | 66% |
| 5 | 244 | 269 | 0 | 4.4 | 4.9 | 91% |
| 6 | 95 | 99 | 2 | 4.5 | 4.7 | 95% |
| 7 | 117 | 158 | 1 | 3.4 | 4.6 | 74% |
| 8 | 206 | 206 | 0 | 4.8 | 4.8 | 100% |
| 9** | 0 | 0 | 0 | 0 | 0 | - |
| 10** | 0 | 0 | 0 | 0 | 0 | - |
| 11 | 126 | 168 | 1 | 3.5 | 4.5 | 78% |
| 12 | 70 | 70 | 0 | 5 | 5 | 100% |
| 13*** | - | - | - | - | - | - |
| Average | 109.1 | 138.6 | 0.9 | 3.8 | 4.8 | 80% |

\* The analysis window= the interval including the lane departure+ 4x2750m intervals.

\*\* No lane departure event observed.

\*\*\* No video data available for drowsiness subjective rating

Figure 15

UNOBTRUSIVE DRIVER DROWSINESS DETECTION SYSTEM AND METHOD

RELATED APPLICATION

This application claims the benefit of U.S. Provisional Application No. 61/193,199, filed Nov. 5, 2008, the entire content of which is incorporated herein by reference.

BACKGROUND OF THE INVENTION

1. Field of the Invention

The present invention relates to a system and method for detecting drowsiness in a driver. More particularly, the present invention is for a drowsy driver detection system with improved detection recognition.

2. Background of the Related Art

Driver drowsiness in commercial truck drivers is a major concern and is responsible for thousands of accidents and fatalities every year. In a 1994 report (Knipling 1994), the Office of Crash Avoidance Research (OCAR) of the National Highway Traffic Safety Administration (NHTSA) identified driver drowsiness as one of the leading causes of single and multiple car accidents. NHTSA estimates that 100,000 crashes annually involve driver fatigue resulting in more than 40,000 injuries. The Fatality Analysis Reporting System (FARS) estimates 1,544 fatalities due to driver drowsiness related accidents, each year. More than 3% of drowsiness related crashes (i.e. a total of 3,300 crashes and 84 fatalities) involved drivers of combination-unit trucks. Based on police reports, drowsiness accounts for 1% to 3% of all U.S. motor vehicle crashes (Lyznicki, Doege et al. 1998). The police report studies are likely to provide substantial underestimate as the drivers involved in fatigue accidents does not admit their state of drowsiness, and police may not investigate fatigue issues due to lack of time and knowledge.

Fatigue has been estimated in 15% of single vehicle fatal truck crashes (Wang and Knipling 1994) and is the most frequent contributor to crashes in which a truck driver is fatally injured (NTSB 1990). Based on NHTSA General Estimates System (GES) statistics (Knipling and Wierwille 1994), although the frequency of drowsiness related crashes involving passenger vehicles is greater than that of combination-unit trucks, the number of involvements per vehicle life cycle for trucks is about 4 times greater due to their very high exposure level, as well as the greater likelihood of night driving. Moreover, truck drowsy driver crashes are more severe in terms of injury and property damage (Wang and Knipling 1994). Long hours of continuous wakefulness, irregular driving schedules, night shifts, sleep disruption or fragmented sleep due to split off-duty time put truck drivers more at risk (Gander and James 1998), (Hamelin 1987), (McCartt, Rohrbaugh et al. 2000).

Driver's drowsiness can be measured by two classes of phenomena: Physical and physiological and Vehicle state variables. Physical and physiological measurements include the measurement of brain wave or Electroencephalogram (EEG) (Akerstedt and Gillberg 1990; Huang, Kuo et al. 1996), eye activity (Skipper, Wierwille et al. 1984; Dingus, Hardee et al. 1985; Ueno, Kaneda et al. 1994; Ogawa and Shimotani 1997). PERCLOS (PERcent eyelid CLOSure) is one of the most widely accepted measures in scientific literature for measurement and detection of drowsiness (Dinges, Mallis et al. 1998; Grace, Byrne et al. 1998).

Drowsiness detection systems have been developed which work based on measurement of Physical and physiological features, and can provide very good detection accuracy. However, they have some shortcomings. The problem with an EEG is that it requires the use of electrodes to be attached to the scalp and that makes it very impractical to use. Eye closure activity can also provide good detection accuracy, but capturing eye image unobtrusively can be expensive and challenging under certain conditions. Changes in light conditions, correction glasses, angle of face, and other conditions can seriously affect the performance of image processing systems.

With respect to Vehicle State Variables Measurement, other approaches for detecting driver drowsiness are based on monitoring driver inputs or vehicle output variables during driving. These methods have the advantage of being non-intrusive to the drivers. In this category, the focus of measurement is not on the condition of the driver, but on the performance output of the vehicle hardware. The vehicle control systems that might be monitored for sensing driving operation include the steering wheel, accelerator, and brake pedal. The vehicle parameters that can be measured include the vehicle speed, acceleration, yaw rate and lateral displacement. Since these techniques allow non-contact detection of drowsiness, they do not give the driver any feeling of discomfort. On the negative side, they are subject to numerous limitations depending on the vehicle type and driving conditions. Wierwille et al. (1992) discussed the performance measures as indicator of driver drowsiness in detail.

Researches indicate variables related to vehicle lane position show good correlation with drowsiness (Skipper, Wierwille et al. 1984), (Dingus, Hardee et al. 1985), (Pilutti and Ulsoy 1997). Since this research uses steering wheel data to detect drivers' drowsiness, this section will focus more on the previous studies and inventions regarding to using steering wheel data to detect drowsiness. Reference (Chaput, Petit et al. 1990) suggests that there exists some correlation between micro steering movements and drop in vigilance. Researchers (Elling and Sherman 1994) reported that steering wheel reversals and standard deviation of steering wheel angle are two measures that show some potential as drowsiness indicators. Other researchers (Fukuda, Akutsu et al. 1995) have developed a driver drowsiness detection system at the Toyota Motor Company. The authors used steering adjustment time to estimate drowsiness. In addition, phase plots of steering wheel angle verses steering wheel velocity can be used as an indicator of drowsiness (Siegmund, King et al. 1996).

A system that relies solely on steering inputs provides a number of benefits over the more common means of detecting drowsiness through eye-tracking or lane departure detection systems. A steering-only detection system is unobtrusive, capable of being implemented inexpensively with a minimal amount of additional sensors and computing power, and immune to problems associated with the dependency of other detection systems to the environment and weather such as performance degradation under low-light or rainy conditions.

A review of steering-based drowsiness detection systems is noted in Hartley, Horberry et al. 2000; Kircher, Uddman et al. 2002. Using vehicle steering activity as an indicator of drowsiness has been cited by many studies. Hulbert (1972) found that the sleep-deprived drivers have a lower frequency of steering reversals (every time steering angle crosses zero degree) than that of rested drivers. Researchers like Mast et al. (1966) and Dureman and Boden (1972) have found that there is a deterioration of steering performance with drowsiness. According to Kahneman (1973), effort and SWRR (Steering Wheel Reversing Rate) are linked. He showed that the SWRR decreases under the influence of substances such as alcohol, which reduces driver activation level. Ryder et al. (1981) found that the frequency of steering reversals decreases with time on task.

Yabuta et al. (1985) hypothesized that when a driver is drowsy or falling asleep his/her steering behavior becomes more erratic. Yabuta defined this erratic steering behavior as "more frequent steering maneuvers during wakeful periods, and no steering correction for a prolonged period of time followed by a jerky motion during drowsy periods." Dingus et al. (1985) found that several steering related measures, such as steering velocity, steering wheel increment, and low velocity steering, can be used to predict drowsiness. Mackie and Wylie (1991) provided a review of patterns of steering wheel movements and vehicle speed. They have affirmed the complexity of the analysis of these two variables and reported that the environmental factors could highly affect the steering precision.

A study conducted by Chaput et al. (1990) suggests that there exists some correlation between micro steering movements and drop in vigilance. During high vigilance (alert) periods small amplitude steering wheel movements are frequent, but during fatigued periods large amplitude movements are more visible. Elling and Sherman (1994) analyzed actual driving data from one-hour of continuous driving by professional drivers. They reported that steering wheel reversals and standard deviation of steering wheel angle are two measures that show some potential as drowsiness indicators. They also reported that gap-size (i.e. the angle that the steering wheel must be reversed before being counted as a reversal) has a major influence on the reversal rate. Their gap-size function has a dead-band that disregards any extremely small reversals such as those due to road variations.

Fukuda et al. (1995) developed a driver drowsiness detection system at the Toyota Motor Company. The authors used steering adjustment time to estimate drowsiness. Their method consists of the following steps: (a) Steering adjustment intervals are calculated at different speeds for alert conditions (learning). These intervals vary with speed and individual behavior but it follows the same pattern. (b) The steering adjustment intervals are normalized at 80 km/hr (50 mph) speed. These intervals are constantly calculated. Whenever it reaches a threshold value, the driver is classified as drowsy. The value of drowsiness threshold is not constant but it varies with speed. The driving threshold is calculated by taking the product of the mean value of learned steering adjustment intervals in the normal state and the mean value of most recent steering adjustment intervals. The results show good correlation with EEG.

Siegmund et al. (1996) conducted an experiment based on the performance of 17 long haul truck drivers under alert and fatigued conditions on a closed circuit track. They presented a steering based set of weighing functions. These functions are based on steering angle and steering velocity. According to the researchers these weighing functions are correlated with EEGs and subjective evaluations of drivers. According to their findings, phase plots of steering wheel angle verses steering wheel velocity can be used as an indicator of drowsiness.

There is an on-going project so called SAVE (System for effective Assessment of the driver state and Vehicle control in Emergency situations) (Brookhuis, de Waard et al. 1998). The project aims to develop a demonstration prototype to identify driver impairment cause and classify it in one of the following categories: fatigue or sleep deprivation, alcohol or drug abuse, sudden illness of the driver and prolonged periods of inattention. The system is claimed to detect 90% of drowsy cases, but there is no formal report on the evaluation of the performance of the system. Sayed and Eskandarian (2001) developed an algorithm, which is based on Artificial Neural Network (ANN) learning of driver steering. They trained an ANN model using data from a driving simulator, driven by human subjects under various levels of sleep deprivation. The model identified drowsy and wake steering behavior, calculated over fixed period of time, with good accuracy.

The Center for Intelligent Systems Research (CISR), at The George Washington University, previously performed a series of experiments to develop a drowsiness detection algorithm, which is based on Artificial Neural Network (ANN) learning of driver's steering (Sayed and Eskandarian 2001; Sayed, Eskandarian et al. 2001a; Sayed, Eskandarian et al. 2001b). The development of the model was based on using the data from a passenger car driving simulator. Their model showed that steering activity can be used among other variables to indicate driver's drowsiness. Due to the difference between the dynamics of trucks as compared to cars and the professional skill level of commercial drivers, the effect of drowsiness on truck driving performance was not clear.

SUMMARY OF THE INVENTION

The inventors of the present invention conducted a new experiment with commercially licensed truck drivers as subjects in the truck driving simulator to gain two major goals. One goal was to develop a new alternative drowsiness detection system and method employing an improved algorithm. The development of the detection algorithm required to meet the challenges arose from the dependency of steering signal to road curvature and vehicle speed. The inventors analyzed and observed the steering wheel signal behaviors of drowsy drivers and identified two distinct drowsiness-related behaviors in all signals. A drowsiness detection system (DDS) was designed to implement a signal processing method so called Empirical Mode Decomposition (EMD) method. EMD is a part of Hilbert Huang Transform (HHT) tool (Huang, Shen et al. 1996; Huang, Wu et al. 2003; Huang and Shen 2005; Flandrin and Goncalves 2004), developed by Huang. HHT is a practical time-frequency analysis tool for non-stationary non-linear signals. Researchers have used this method in variety of applications (Huang, Wu et al. 2003). However, this is the first use of EMD in drowsiness detection domain. The detection method uses a decomposed component of the steering wheel signal to extract specific features representing the steering control degradation phases. The algorithm is able to classify the measured features into alert or drowsy state.

Accordingly, the present invention is an unobtrusive drowsiness detection system for commercial drivers as well as drivers of passenger cars. This system uses only steering data for the detection algorithm and can detect drowsiness timely and accurately. The new detection method provides a reliable and robust drowsiness detection method. This system avoids and reduces fatalities, drowsiness related injuries, and property damages. The detection system addresses a number of challenges.

One challenge faced by the present invention is human steering control variability. Naturally, each driver has his/her own individual style of driving and vehicle control. Some drivers are sensitive to lane position variations and make more small amplitude steering corrections to keep the vehicle in lane. Other drivers are careless to their lane keepings and make less steering corrections with larger amplitude resulting in larger variations of their lane keeping performance. Therefore, a detection system using any steering control-related variable has to be capable of handling variability in steering control behavior to adapt the system with respect to different drivers.

Another challenge faced by the present invention is the vehicle steering variability between passenger cars and trucks. Due to differences in vehicle dynamics and steering feel between passenger cars and trucks, steering ranges and variability are different between these two vehicles. Therefore, the development of a drowsiness detection system based on steering wheel data for one type of vehicle does not guarantee that it will work for the other type. These differences also affect other steering related variables.

A third challenge is dependency of steering-based methods on road geometry. One of the major obstacles in using steering wheel data for drowsiness detection is the dependency of steering values on road geometry and curvature. This requires techniques that can eliminate the curvature from the steering data or handle the data independently of the road geometry. A fourth challenge is accuracy and reliability. The detection system has to be in a level of performance that can predict drowsy related hazardous events accurately and timely with the minimum rate of missed and false alarms. A fifth challenge is comfort. The goal of driver assistant systems is to increase safety and decrease driver mental load which causes distraction and discomfort. Therefore, non-intrusive methods can get higher satisfaction rate among drivers. A sixth challenge is robustness. The detection system should be robust for various driving scenarios and able to distinguish non-drowsy changes in vehicle control variables from drowsy-related variations. It should also be capable of handling different driving scenarios in different environments, i.e. various weather, road type, and speed limit conditions.

In accordance with these and other goals and objectives, the present invention is a drowsiness detection system and method that addresses this severe problem, especially for commercial truck drivers who are at higher risk as compared to passenger car drivers. This system contains the following unique contributions: identification of unique patterns in steering signals that are indicative of driver drowsiness; development of a new unobtrusive drowsiness detection method using only steering wheel angle data; and testing and evaluation of the new unobtrusive drowsiness detection algorithm on commercial drivers in a truck simulator environment.

Commercial professional drivers were tested under different levels of sleep deprivation in a truck simulator. Driver behavior and vehicle driving performance parameters were recorded. A total of thirteen subjects completed the study. Each driver's level of drowsiness was carefully observed and rated through video data and eye tracking data. The simulation data showed that drowsiness has significant effect on lane keeping and steering controls. The data also shows a two-phase degradation of steering control for drowsy drivers in which large steering corrections are combined with no steering wheel position change during dozing off periods. These phases are captured automatically by the new drowsiness detection method.

The drowsiness detection technique of the present invention is based on identifying steering control degradations due to drowsiness. The system uses a signal decomposition technique, called Empirical Mode Decomposition (EMD), on measured steering wheel signals. The detection method uses a decomposed component of the steering wheel signal to extract specific drowsiness-affected features. These features represent the steering control degradation phases which were identified during the steering data analysis. The present invention is able to classify the measured features into alert or drowsy state. It is not dependent on the road geometry information and can automatically compensate steering control performance variability between drivers. Testing results in a truck driving simulator show that the system is accurate in detecting the drowsy periods and drowsy-related lane departure events. The detection method is unobtrusive, can be applied on-line, and is highly accurate. The system is implemented in a vehicle during driving by using proper sensors (to continuously measure the steering wheel angle and store this data for a period of time). The detection operation can be implemented by a separate processor, or incorporated into existing in-vehicle CPUs or computers which use the sensed steering wheel data, processes the data in real-time, and determines a drowsy (or alert) state continuously. The processor sends an alert signal to an alarm device when it determines that the driver is drowsy, to alert the driver or passengers.

BRIEF DESCRIPTION OF THE FIGURES

FIG. 15 is a table showing performance analysis of the present invention, 11,000 m/6 min before lane departures caused by drowsiness (SEVD>0)

DETAILED DESCRIPTION OF THE PREFERRED EMBODIMENTS

Figures 1A, 1B:
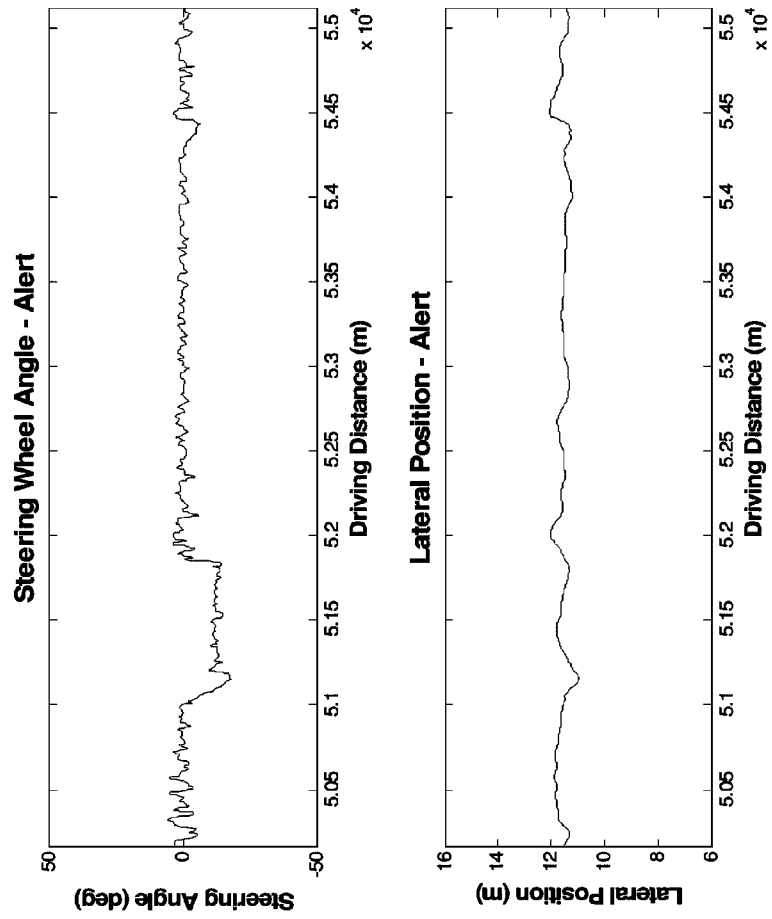
FIGS. 1(a)-(d) are plots of a sample of degradation phases before a crash compared with the data of alert driving for the same segment of the road.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents that operate in similar manner to accomplish a similar purpose.

The primary factors of driver drowsiness are the sleep-wake cycle and the amount of wakefulness. The likelihood of drowsiness onset and dozing off is higher during sleep cycle or night sessions. Drowsiness is identified and validated in two ways: (a) Eye Closure Measures (PERCLOS), and (b) Subjective Drowsiness Rating. The Eye Closure Measures (PERCLOS) of drowsiness indicates the intervals of time the eyes were closed. PERCLOS (PERcent eyelid CLOSure) is the percentage of time the eye is more than 80% closed (Dinges, Mallis et al. 1998; Grace, Byrne et al. 1998).

Under Subjective Drowsiness Rating (SDR), drowsiness can be rated by video recordings observation and real-time surveillance of video cameras during testing from each driver's face, and identified based on subjective judgment from drowsy facial attributes and eye closure observation. The subjective assessment of drowsiness level was based on a five-level rating scale: (i) SDR 0: alert, (ii) SDR 1: questionable, some primary signs of fatigue and drowsiness were detected, i.e. sighing, (iii) SDR 2: moderately drowsy, the eye closure was slower and longer, (iv) SDR 3: very drowsy, the driver experienced doze-off, and (v) SDR 4: extremely drowsy, the driver was completely asleep. Although SDR is a good indicator of the level of drowsiness, it cannot correctly represent the severity of the drowsiness. To this extent, another variable, Severity of Drowsiness (SEVD), was defined to be the total time while SDR>3 divided by the driving time.

It was determined that sleep deprivation significantly degraded lane keeping and steering performance. There were three variables showing the degradation, namely steering wheel angle signal power, standard deviation of steering wheel angle and standard deviation of lateral displacement. The steering wheel angle power refers to the "power of a signal," and is used here to refer to the average of the squared steering angle. The square steering angle is used to measure variances without the regard for its sign, i.e., negative or positive. The angle is defined from the center position of the wheel. The lateral displacement is the deviation of a vehicle from a lane centerline. The lateral displacement can be determined during testing in a driving simulator, and is used to determine the algorithm for detecting drowsiness based on steering angle only. Lateral displacement can also be determined based on a lane departure warning system, which determines lane position with the use of camera vision systems.

There is a significant difference for standard deviation of lateral displacement between morning and night conditions (F=15.31, P=0.001), where F and P are statistical measures, showing a numerical value (F) (or also known as "F-test" in statistics) for similarity or dissimilarity of two measured variables with a confidence level above or below (depending on how the hypothesis is worded) of certain level (P). F and P are values of statistical tests of two variables. These variables are measured or calculated, e.g., steering wheel angle power (as described above), or the standard deviation of steering angle, or any other selected variable. Instead of qualitatively saying how a variable is different for drowsy vs. a non-drowsy driving, these statistical tests of the measured variable indicate a quantitative measure of that difference. Therefore, the indicated numbers F and P are statistical measures of the listed variable (e.g. power and standard deviation). Also, the statistical analysis showed a significant increase in steering wheel signal power (F=13.16, P=0.002) and standard deviation of steering angle (F=19.62, P<0.001) for night sessions. For successful one-to-one correlation of steering performance with drowsiness, the effect of road curvature is removed from the steering data. Regression analysis showed that the standard deviation of lateral displacement, steering power, and standard deviation of steering had significant effect on the numbers of crashes, whereas speed displayed no significant effect.

Two Phases

It was further determined that, based on steering and lateral displacement signals, drowsiness degrades steering-related performance in two phases. The first phase is the "Impaired" phase (Phase-I), where the driver decision making ability is affected. The driver cannot smoothly follow the desired trajectory. As a result, the driver performs a zigzag driving. This effect is caused by steering over-correction and is observed on and off for a certain period of time before dozing off incidents. This phenomenon can be identified as large variations in vehicle lateral position and large amplitudes in steering wheel angle signals. The second phase, or "Dozing off" phase (Phase-II), is when the driver provides no corrective feedback and the vehicle continues its path without any correction. This can be traced by a constant steering angle value over a short period of time (smaller variability in steering wheel angle) combined with increasing lateral displacement and ultimately lane departure. It was determined that most vehicle run-off road crashes occurred during this phase.

Figures 1C, 1D:
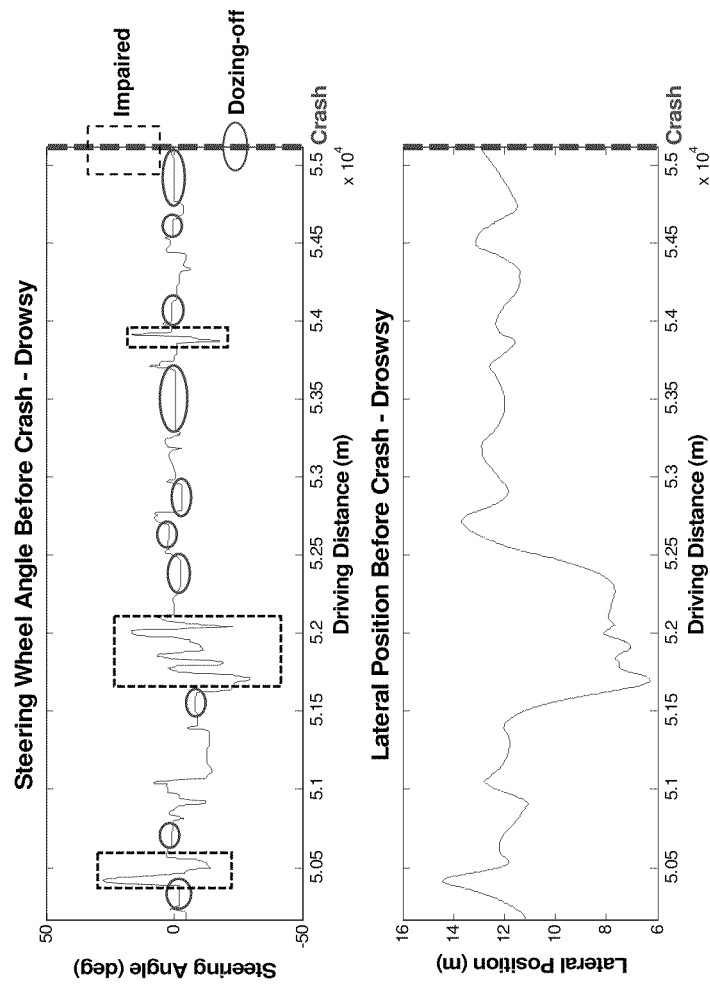

FIGS. 1(a)-1(d) highlight a sample of these phases for a driver. FIGS. 1(a) and 1(b) illustrate the steering and lateral displacement data for the alert data, whereas FIGS. 1(c) and 1(d) show the drowsy data for before the crash for the same segment of the road. In FIG. 1(c), the Impaired phase periods are enclosed in a rectangle, and the Dozing-off phases are enclosed in an ellipse. A Dozing-off phase is shown just prior to the crash. There were also some other constant steering intervals following a sudden steering move, the so-called drift and jerk. Drift and jerk phenomenon is the result of a quick recovery from a doze-off to avoid a crash.

The Drowsiness Detection Algorithm

Figure 2:
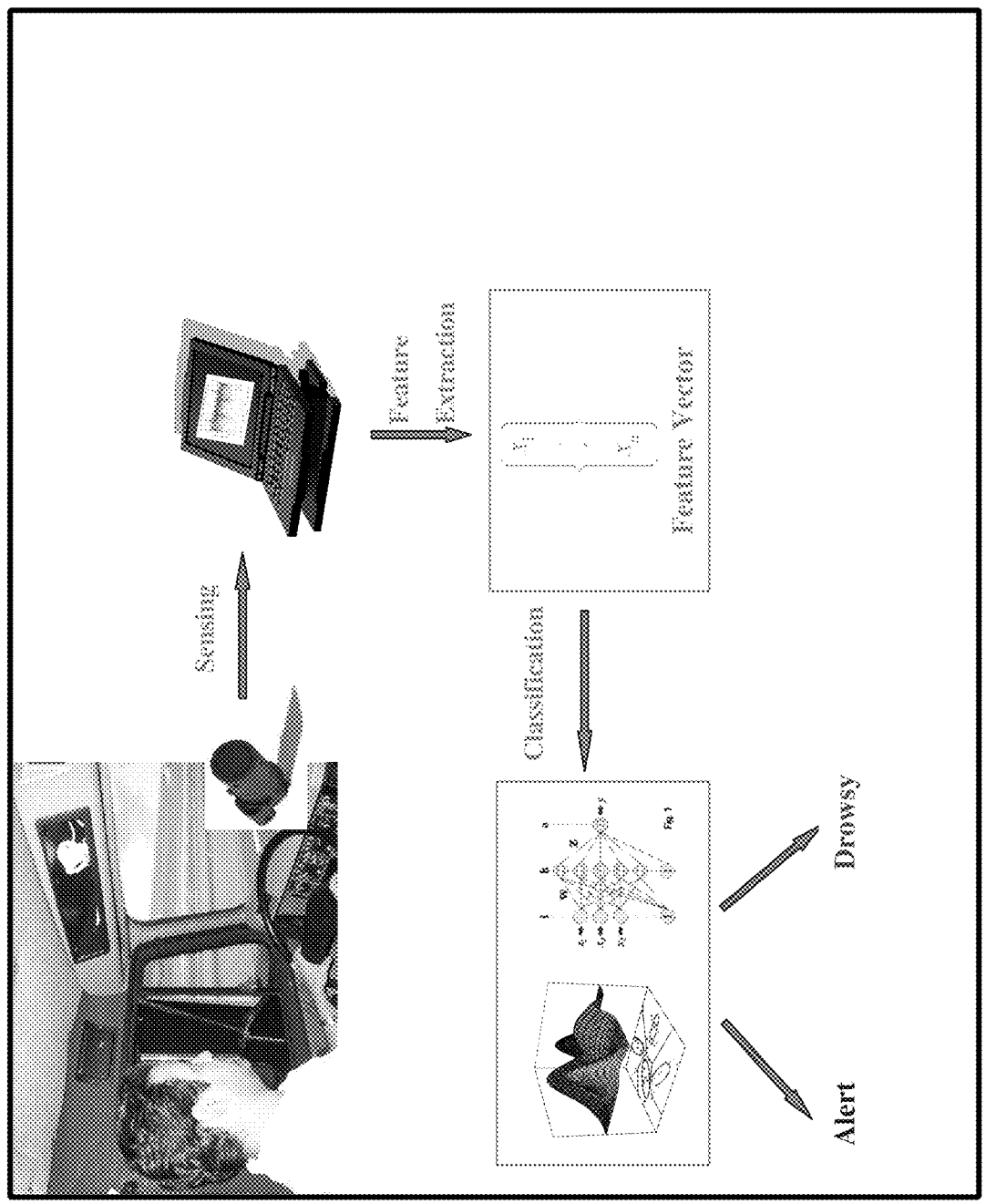
FIG. 2 is a schematic of a pattern classification approach to the drowsiness detection.
Figure 3:
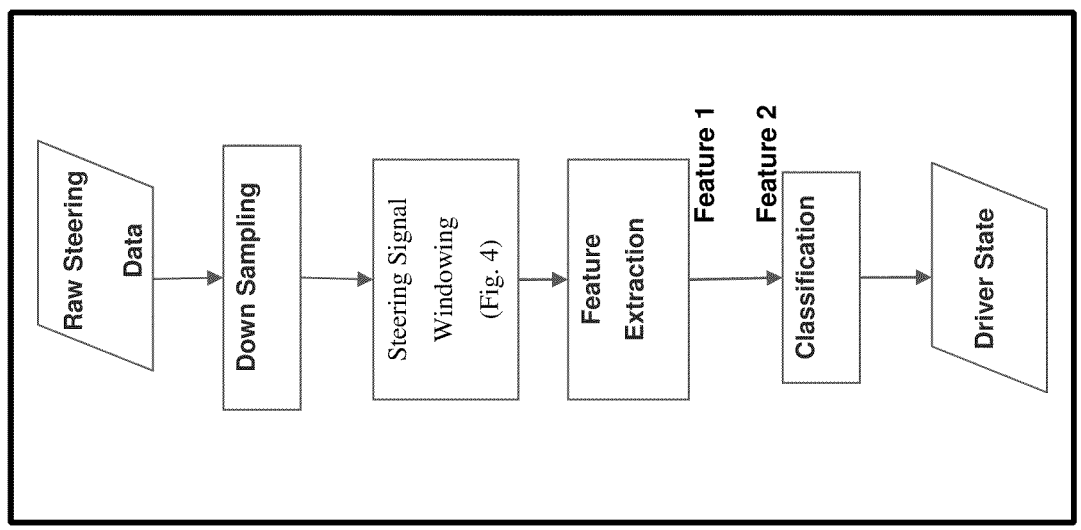
FIG. 3 is a flow diagram of the overview of the detection system.

The objective of this system is to use only steering wheel data to classify the state of a driver into two categories: alert or drowsy. In accordance with the preferred embodiment, the impaired phase and the dozing off phase are both considered to be indications of a drowsy driver. A pattern classification (recognition) approach was utilized to address the problem. FIG. 2 shows the system of the present invention utilized to implement a pattern classification approach for a drowsiness detection problem. The system generally includes a sensor installed on the steering wheel of the vehicle and a processor (shown by a personal computer (PC)). The sensor measures the raw steering wheel data, which is then communicated to the processor. The processor preprocesses the raw steering wheel data. The measured data (raw data) is the steering angle which is measured by a sensor placed in the steering column. This data is stored in a memory every 15 seconds, and processed according to the signal processing method. As shown in FIG. 3, feature extraction and classification are two integrated parts of the algorithm which come after the windowing process.

The preprocessed data is then passed to a feature extractor module, which reduces the data by measuring specific features and properties. The feature extractor extracts specific parameters/evidences from the steering signal, which represent effects of drowsiness on driver's steering control behavior. These effects are identified as degradation phases in steering data. Then, a classifier uses the evidences, presented by the extracted features, to decide the true state of nature. So, the classifier decides whether the driver is drowsy or alert.

In general, the system identifies drowsiness based on the characteristics (features) extracted from blocks of steering data collected over definite periods of time. The system looks into the behavior/trend of extracted features to determine the status of the driver. As best shown in FIG. 3, the detection algorithm consisted of 4 main modules, namely down-sampling, windowing, feature extraction, and classification. The first module is called the down-sampling module. The sampling frequency of measured data was not uniform through the experiment (10-15 Hz). In the first step, the raw steering data is down-sampled and the analysis sampling frequency was unified ($f_{sampling}$=10 Hz).

The sampling is first a function of the sensor which measures the raw data (i.e., the steering angle). In this sense, the sampling frequency refers to a capability of the sensor to sample data at a certain frequency. For example, a sampling rate of 1 HZ means that the sensor is only able to measure one value per second, or a sampling rate of 10 means the sensor is capable to provide 10 values per second. Of course the higher the sampling rate or the frequency of data, the more sophisticated the sensor. But there are limitations for some sensors.

Sampling rate or frequency is important in analyzing the steering angle data. The fine (micro) motions of steering to the left and right happens in millisecond. To have a millisecond data means you need a sensor which can collect 1,000 data points per second, i.e. a sampling rate of 1000 HZ. However this may not be realistic both in terms of sensor capability and also in real time processing of this amount of data (i.e., going through our entire signal calculations). A sensor sampling rate of at least about 10 HZ is sufficient for the present invention. If a higher rate of sampling is provided by the sensor, then a down sampling can be utilized to synchronize the processor with the sensor. Of course, the sensor and processor preferably operate at the same sampling rate, so that down-sampling may not be needed at all.

Figure 4:
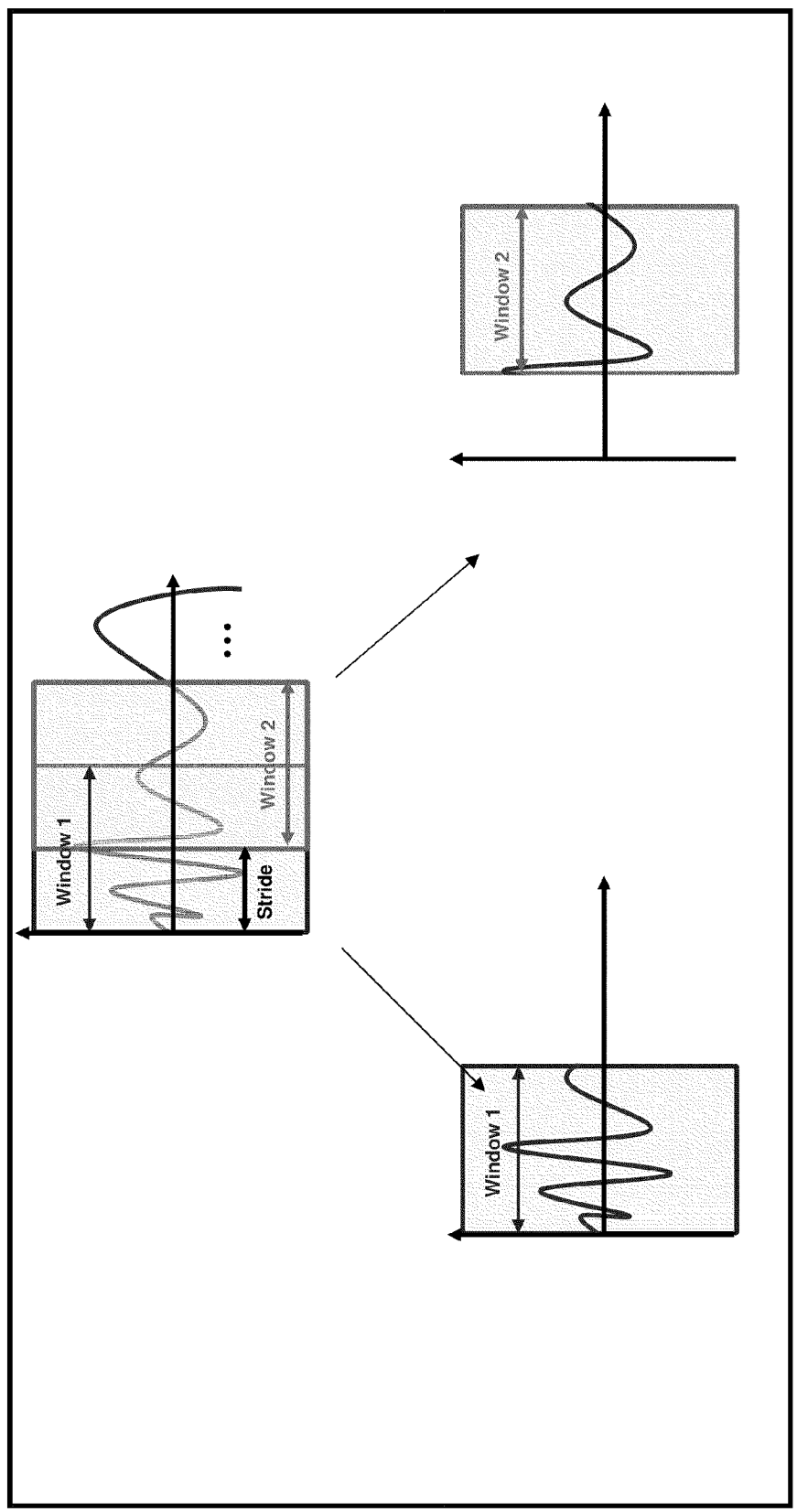
FIG. 4 is a diagram showing overlapped signal windowing.

Continuing with FIG. 3, once the information is down-sampled, it is passed to the Windowing module. Windowing is the part of the signal processing scheme which provides overlapping information about the time history of the drivers steering and brings out the relevance of the signal. To analyze the data, the entire recorded steering angle signal for each experiment was divided into consecutive sequences of data frames (windows). The process of breaking the recorded data into smaller frames is referred to as data/signal windowing, which is shown in FIG. 4. This action is analogous to the real time recording of data in which the data are recorded (i.e., the sensor continuously gives the data and a storage unit (which can be supplied with the sensor module, for instance) stores this data for a period of time which is function of the sensor or CPU's storage capability) and analyzed over a period of time. The period of time is preferably at least 8-15 seconds of driving/steering intervals depending on the processing speeds.

Referring back to FIG. 3, the Feature Extraction module follows the Steering Signal Windowing module. One of the challenges in developing a drowsiness detection system that uses steering activity is the dependency of the steering wheel signal to road geometry and curvature. Most of the systems that use steering wheel activity to detect drowsiness, preprocess the steering signals to eliminate the road curvature effect on the steering signal. These algorithms leverage empirical methods or prior knowledge of the road geometry to eliminate the effect. A primary goal in developing the present algorithm was to come up with a system that identifies both the degradation phases in the steering signal without implementing an empirical road curvature elimination preprocessing.

To address the problem, the feature extraction module utilizes a signal processing method so-called Empirical Mode Decomposition (EMD). By implementing an EMD algorithm, the steering signal is decomposed into different intrinsic signals or basis signals. A intrinsic signal was chosen and the effect of drowsiness on steering wheel signal was modeled by measuring two statistical parameters. A signal can be decomposed into different basis signals called Intrinsic Mode Functions (IMF). The summation of these functions can reproduce the original signal, which means $$x(t) = \sum_{j=1}^{n} c_j + r_n$$

where Cj is the IMFj.

The final module is the Classification module. The extracted features are classified by a classifier. In this approach, a k-nearest neighbor classifier is used.

Figure 5:
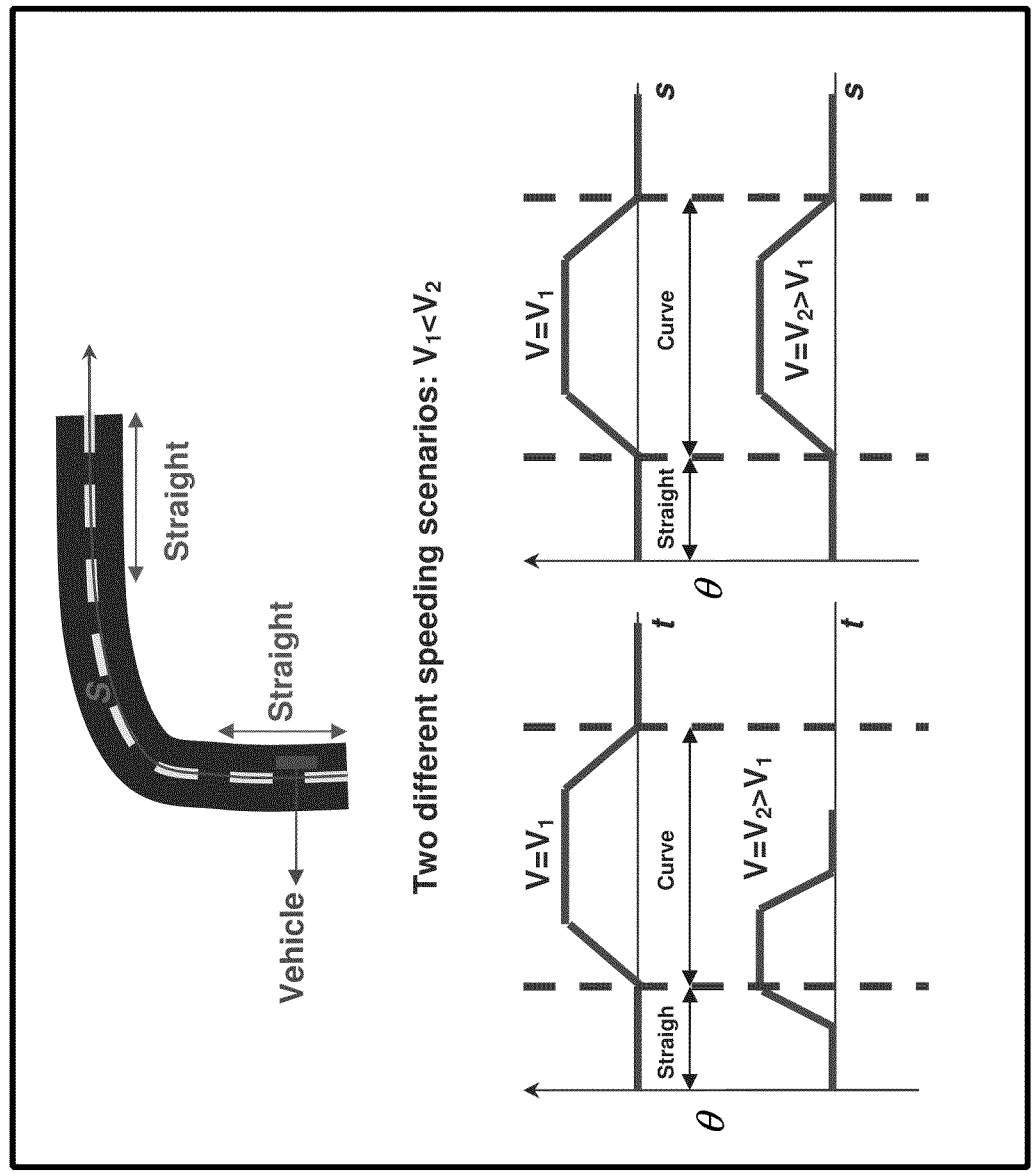
FIG. 5 shows the effect of speed on steering signal.

Several challenges are addressed by the use of the drowsiness detection algorithm in the current detection system and method. One issue that is addressed is the vehicle speed. The number of steering corrections over a fixed time interval is dependent on the vehicle speed. For example, FIG. 5 displays schematic plots of steering wheel angle versus time, θ(t), and versus driving distance, θ(s), for different speed scenarios ($V_2 > V_1$). In this example, the road geometry consists of sequences of straight, curve and straight segments. According to the plots, the θ(t) signal is shorter for the faster vehicle, while the θ(s) signal does not differ for different driving speed. The dependency of θ(t) to vehicle speed can result different frequency behavior of the steering signal for different vehicle speed levels for a similar situation (road configuration). The steering signal was analyzed with respect to road distance, θ(s) which is a simplified assumption to incorporate speed into steering angle-time analysis of the data.

Another issue addressed by the current invention is the effect of road geometry on steering. Steering based drowsiness detection algorithms are dependent on road curvature and geometry. Therefore, the performance of the system is directly dependent on handling/eliminating the curvature effect. Most of these detection methods implement a preprocessor which eliminates the curvature effect. These preprocessors mainly use prior knowledge of the road geometry or empirical methods to eliminate road curvature effect.

The current invention is able to identify the two important drowsiness degradation phases, Phase-I (Impaired) and Phase-II (Dozing Off), in steering control which characterize the drowsy behavior of a driver. If either of these phases are detected, then the system considers the driver to be drowsy, and the alarm is sounded.

Another issue addressed by the current invention is the variability in steering behavior. Some drivers prefer to drive with small steering corrections, while others are less sensitive to their lane keeping and make larger steering movement (higher amplitude). In addition, drivers are different in responding to initializing steering corrections. Some have longer response time to turn the steering wheel to correct the vehicle heading angle and keep it in the lane. Moreover, due to differences in vehicle dynamics and steering feel among different vehicles, steering ranges and variability vary from vehicle to vehicle. As a result, a detection system needs to be robust to different driver steering control behavior.

To address these and other issues, and in summary of the descriptions above, several technical steps were taken to develop the drowsiness detection system. First, the effect of drowsiness on steering wheel control was identified. The steering data of drowsy drivers was analyzed and correlations were determined between the subjective ratings (SEVD, etc.), i.e. indicators if a person is drowsy and at what level, and the steering angle time histories or signals (the entire dynamic of a signal, its amplitude, frequency, and all other characteristics). Second, the use of steering wheel signal for detecting drowsiness, i.e. dependency of the steering signal pattern to road curvature and vehicle speed, was determined. Third, the proper features/evidences were extracted from the steering signal to present the effects of drowsiness on steering control. And fourth, a classifier was utilized to identify the state of driver, i.e. alert or drowsy.

Empirical Mode Decomposition

The current invention represents a signal in terms of Amplitude Modulation (AM) and Frequency Modulation (FM). Each intrinsic mode is representing a simple oscillation with equal number of extrema and zero-crossings. The examination of the steering data on curves identified two different time scale characteristics. Empirical Mode Decomposition is based on the assumptions that the analyzed signal has at least two extrema, and that the characteristic time scale is defined by the time lapse between extrema. The goal is to represent a signal in terms of different intrinsic modes with simple oscillation. Each mode, so-called Intrinsic Mode Function (IMF), has the same number of maxima and zero-crossings. (They can differ at most by one.) In addition, at any point of an IMF signal, the mean value of the envelope passing through maxima (upper envelope) and the envelope passing through minima (lower envelope) is zero.

The process of IMF functions extraction is called sifting. A signal, $x(t)$, can be decomposed into n IMFs ($c_j$) in a way that $$x(t) = \sum_{j=1}^{n} c_j + r_n$$

where $r_n$ is the signal trend or a constant and $c_j$ is the $j^{th}$ IMF.

Figure 6:
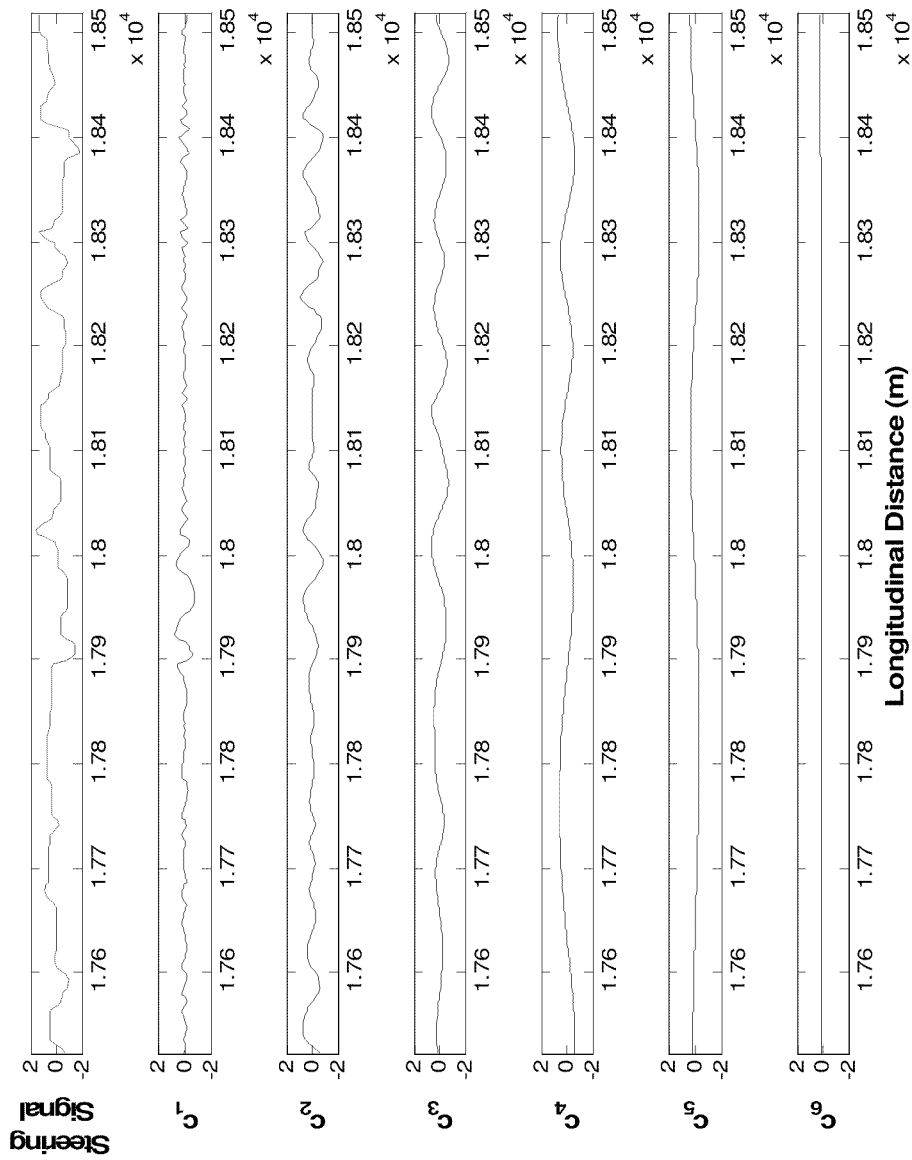
FIG. 6 are graphs showing a sample of decomposed steering signal using EMD.

FIG. 6 shows a sample of decomposed normal steering wheel signal using EMD. The steering angle signal is assumed to be a function of driving distance for EMD analysis. That assumption simplifies the calculation of normalizing the effect of speed on steering wheel angle signal. The figure shows that the IMFs with smaller index number (i.e., $c_1$) represent higher frequency oscillation mode of a waveform, while the IMFs with larger index number (i.e., $c_5$) show the lower frequency behavior of the waveform.

Signal decomposition, and in particular, the EMD signal processing, is well-suited for the steering wheel signal since it is a non-stationary non-linear signal (with unpredictable/stochastic behavior). The non-stationary signal is a signal that its statistical parameters change with time. The EMD decomposes the signal into a posteriori-defined basis, and is an adaptive method derived from the data. The basic assumption is that any data comprises different intrinsic modes of oscillation. In summary, this means that the signal is fast oscillation super imposed to slow oscillations. The outcomes of the EMD algorithm are a set of intrinsic mode functions. Each intrinsic mode represents a simple oscillation with equal number of extrema and zero-crossings.

Based on the truck experiment data, the steering signal behavior is nonstationary and nonlinear, which are the characteristics of a natural signal. The steering signal comprises two types of corrections: lane keeping corrections and curve negotiation corrections. As a result, in situations when a vehicle is negotiating a curve, the steering wheel angle signal consists of a lane keeping waveform, with high frequency oscillations and zero mean, and a curve negotiation waveform, with low frequency oscillations. The latter waveform is referred as the signal trend. Therefore, ideally if the curvature effect is eliminated, the steering signal should be like a waveform oscillating symmetrically about zero. This is similar to a driving scenario on a straight road (ignoring the lane change). The ideal goal is to transform the original signal into a new space with a symmetric oscillation and no riding waves. The mentioned properties are exactly the EMD components (IMFs) characteristics (like sine waves and the number of extrema and zero crossings are equal. The frequency can be measured using the distance between two consecutive zero crossings).

Therefore, EMD is used to process the data features extraction and preprocessing for steering signal. This works better than other curve removal methods since no assumption is made, and the method works independent of the road geometry. The process of extracting IMFs in EMD method is called sifting:

(1) Identify the local maxima and minima of $x(t)$.

(2) Interpolate the maxima and the minima separately by fitting a spline line. The interpolations will generate an upper envelope ($env_{max}$) and lower envelope ($env_{min}$). The upper and lower envelopes have to cover all the data between them.

(3) Compute the mean values of the upper and lower envelopes $m_1 = (env_{max} + env_{min})/2$. Calculate the residue, that is $h_1 = x(t) - m_1$.

(4) Go back to step 1 and continue the calculations for $h_1$. Therefore, at the $i^{th}$ iteration $h_{1(i-1)} = x(t) - m_{1(i-1)}$. Stop the iteration (after k steps) when all the points of $m_{1k}$ are zero.

(5) The first IMf ($c_1$) is designated as (FIG. 5-9) $c_1 = h_{1(k-1)}$.

(6) Separate $c_1$ from the $x(t)$, and calculate the residue; that is $r_1 = x(t) - c_1$.

(7) Start the sifting process for the residue, $r_1$. $r_1$ is now treated as a new data set.

(8) The procedure is repeated for all subsequent $r_j$'s, where $r_j = r_{(j-1)} - c_{(j-1)}$.

(9) The sifting process can stop (after n steps) either when $c_n$(IMFn) or the residue, $r_n$, becomes smaller than a predetermined condition or the residue becomes a monotonic function from which no IMF can be extracted.

(10) Intuitively, the last residue of the sifting process of a signal represents its trend. The signal is now decomposed. We can obtain $$x(t) = \sum_{j=1}^{n} c_j + r_n,$$

where $r_n$ is the signal trend or a constant.

Feature Extraction

One of the major challenges in the development of the drowsiness detection method is to extract features from the steering wheel angle signals. The extracted features have to be independent of road curvature and representative of the two steering control degradation phases that were observed for drowsy drivers. A steering wheel signal comprises of two types of corrections: lane keeping corrections and curve negotiation corrections. As a result, in situations when a vehicle is negotiating a curve, the steering wheel angle signal consists of two waveforms: a lane keeping waveform, with high frequency oscillations (micro-corrections) and zero mean, and a curve negotiation waveform, with low frequency oscillations.

The curve negotiation waveform is referred to as a curve negotiation trend. If the curvature effect is eliminated, the steering signal should be like a waveform oscillating about zero. This is analogous to a driving scenario on a straight road (ignoring the lane change). By decomposing a signal using EMD, the signal's trend due to curve negotiation was excluded by dealing only with a selected decomposed signal which represents drivers' lane keeping control. In addition, desired features were extracted presenting the two phases of steering control degradations. The first IMF was the point of attention since it represents high frequency behavior of a steering signal known as micro-corrections. Thus, the first IMF is a calculated function that represents a characteristic or a feature of a signal, namely, the low index IMF represents the high frequency signal which is associated with drivers micro corrections. Given the fact that drowsiness can diminish micro steering corrections, the effect of drowsiness on the first IMF was investigated. The goal was to observe the two phases of steering control degradation effects on the first IMF.

The distance between two consecutive zero-crossings (where the signal values are zero) is referred as distance of zero crossings. As explained previously, the number of extrema is equal to the number of zero crossings in each extracted IMF. Therefore, distance of zero crossings can present local frequency characteristic of an IMF, analogous to definition of frequency for a sine wave. In a given interval, smaller distance of zero crossing shows faster oscillation of the signal. The length of zero crossing of the IMF provides an indication of being in phase II dose off period. So instead of monitoring the time history of a signal in a memory (aside from other signal processing calculation), the present invention automatically performs the IMF calculations and reveals this characteristic (also called a feature) of the steering.

Introduction of Two New Features

The effect of the two steering control degradation phases on the first IMF is now discussed, as well as the introduction of two features that are implemented in the detection system. We looked into the first IMF of steering signals of drowsy drivers and traced the two degradation phases as one of two patterns. The first pattern was for the Impaired Phase (Phase-I). During Phase-I, the steering signal has larger amplitude steering corrections (over-corrections). Consequently, a similar effect on an IMF-1 signal was detected. The second pattern was for the Dozing-Off Phase (Phase-II). Longer distance of zero crossings is observed during Phase-II.

The constant value interval of the steering wheel signal during dozing off periods can be inferred as the intervals when the local frequency is zero. The constant value is when the steering angle is not changed and fixed at a constant value because the driver is asleep (dosed off) and is not steering; the length varies depending on driver, conditions, etc. and what is important is that the algorithm of the present invention determines this up as soon as it happens. Since the value of this signal is constant, i.e. the signal is not oscillating, it is when the local frequency of the signal is zero (a straight horizontal line has a local frequency of zero). This characteristic was detected as a relative large scale oscillation in IMF1 components. Thus, if the IMF is calculated and it shows a large oscillation, then it is an indication of constant steering, which is in turn an indication of dose off period of the driver. In addition, longer distances of zero-crossings are expected for the intervals with slower corrections (low local frequencies).

Figure 7:
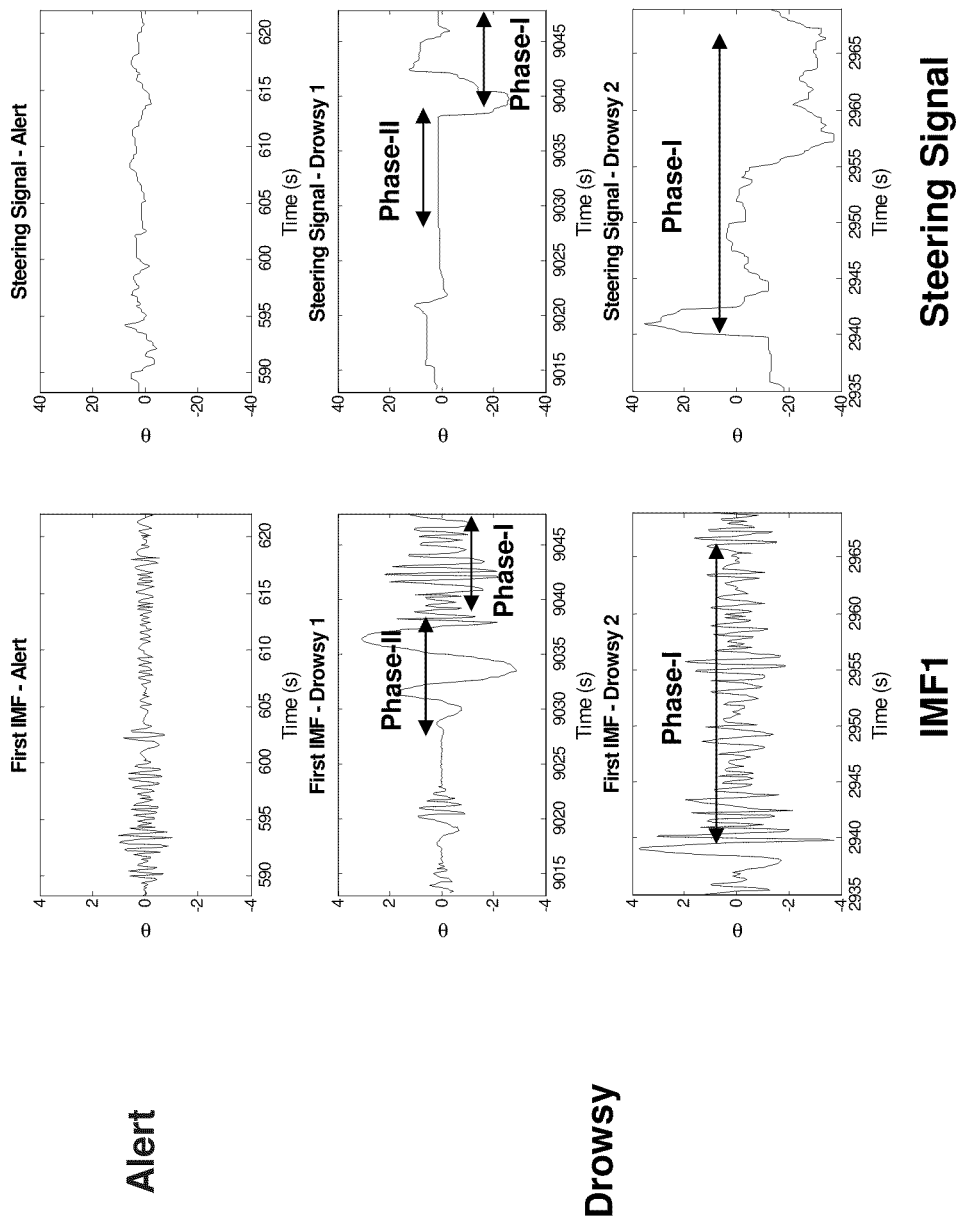
FIG. 7 is a set of graphs showing examples of the effect of drowsiness on IMF-1 (the ordinate range for the first IMF and the signal are different)

FIG. 7 shows examples of IMF-1 signals that are affected by different phases of drowsiness degradation and compares them with an alert signal. The effect of each phase is also marked on the IMF-1 plots. Two types of features were extracted from the steering signal and examined to observe the reflection of the drowsiness on the steering signal. Each feature represents one phase of steering degradation. For instance, taking the middle figures, the raw steering signal data (right graph) shows that during Phase-I, the driver is making micro-corrections, which is represented by the high-frequency signals of the IMF1 graph (left graph). For Phase-II, the raw steering signal shows that the driver is not moving the steering wheel, which is represented by the low frequency in the IMF1 graph.

Figure 8:
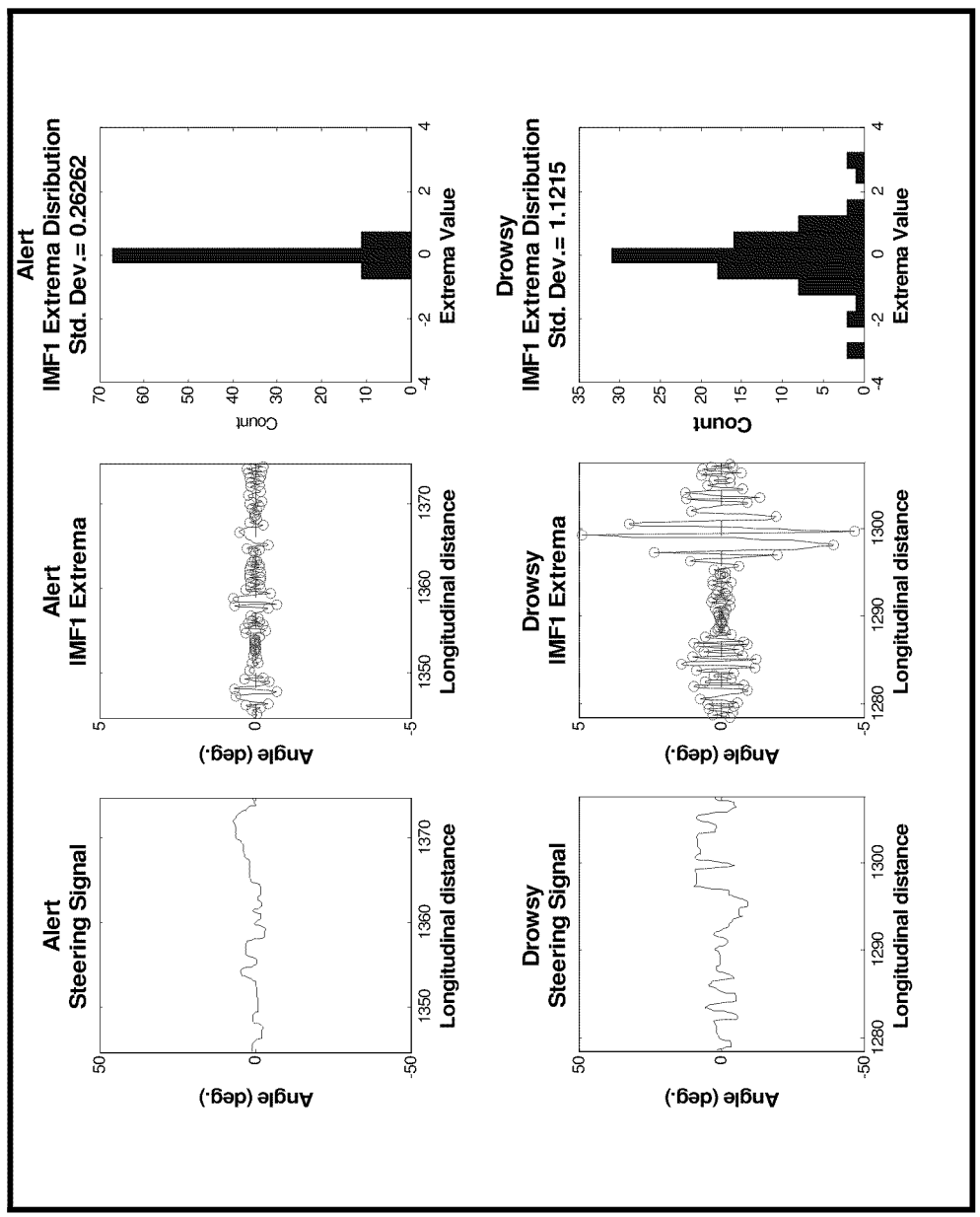
FIGS. 8(a) and (b) are graphs showing samples of IMF1 distributions for alert (SEVD=0) and drowsy (SEVD>0.5) state.
Figure 8B:
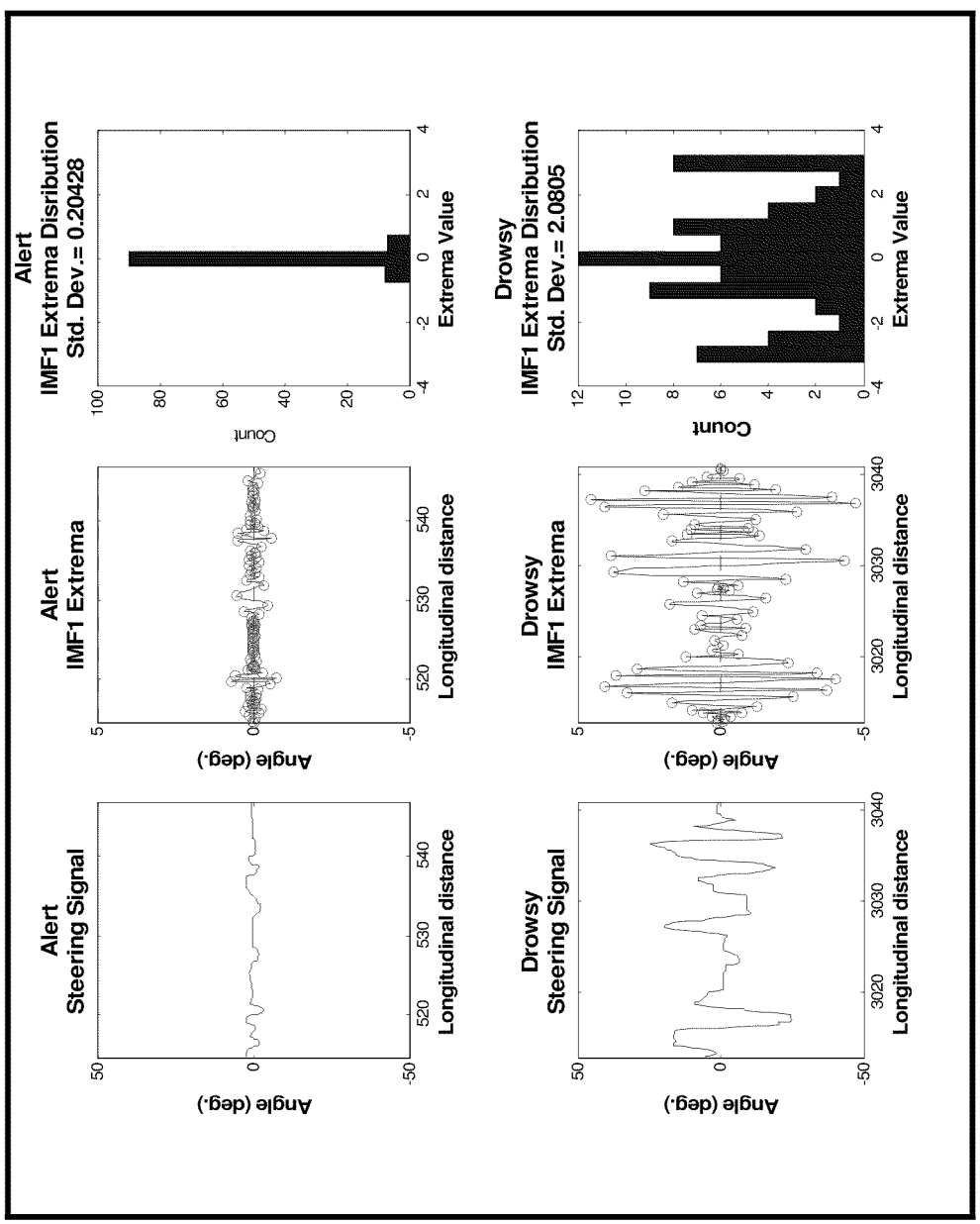

The first extracted feature was Standard Deviation of IMF-1 Extrema (SDIE). This feature assesses Phase-I steering control degradation, the over-steering behavior of a drowsy driver. For periods when SEVD>0.5, the distribution of the IMF-1 extrema values (as well as the standard deviation of the distribution) were analyzed and compared with the alert (SEVD=0) data. Two samples of the data observation are shown in FIG. 8. The analysis of the results showed the fact that, for the periods with large steering corrections, Standard Deviation of IMF-1 Extrema absolute values (SDIE) extracted from drowsy intervals were generally greater than the SDIE values extracted from normal driving intervals. The third column of plots in FIG. 8 show the distribution of the extrema value of IMF-1 for normal vs. drowsy driving. Above the same plots the standard deviation of IMF-1 extrema values are shown, namely 0.26262 for normal driving vs. 1.1215 for drowsy driving. This was an indication that SDIE was a good feature selection which could characterize and quantify over-correction steering behavior.

Figure 9:
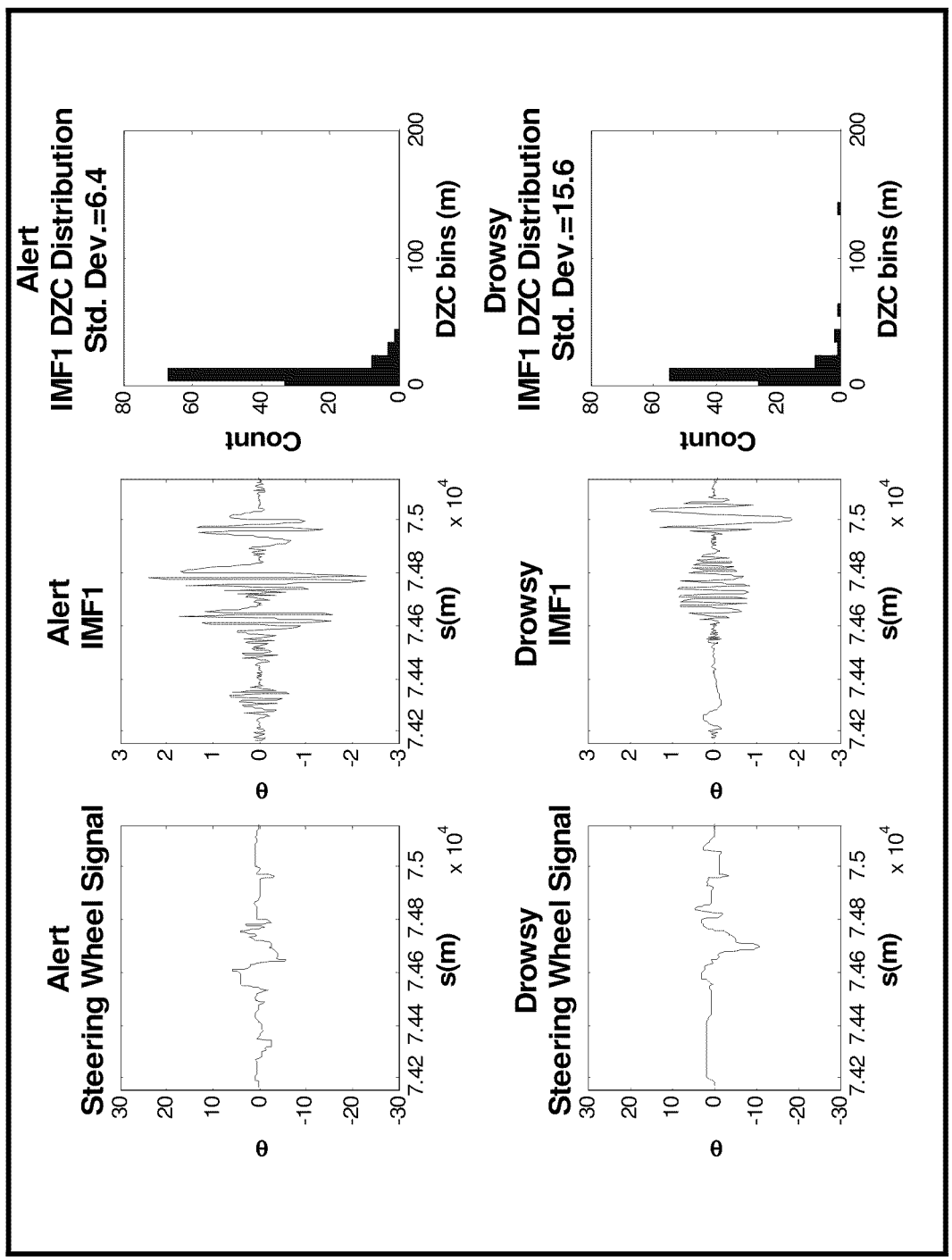
FIG. 9 is a set of graphs for two samples of IMF1 distances of zero crossings (DZC) distribution and its standard deviation for alert and dozing-off driving states.

The second extracted feature is the Standard Deviation of IMF1 Distances of Zero-Crossings (SDZC). The effect of Phase-II phenomenon can be detected as large distance of zero crossings (DZC) in IMF-1 signals. We analyzed distribution of distances of zero crossings values for dozing-off intervals. The standard deviation of DZC was generally higher than the corresponding values for alert driving states. FIG. 9 shows the distributions and standard deviation values for two samples. FIG. 9 clearly shows how the IMF 1 of a drowsy driver steering signal differ from the IMF 1 of an alert driving signal. The third set of plots in FIG. 9 show the IMF 1 DZC distribution and the corresponding standard deviation. The SDZ of IMF 1 signals for drowsy driver is larger than the corresponding values of the alert driver. This is true for all other sets analyzed. Therefore, the standard deviation of distance of zero crossings (DZC) of IMF 1 is a clear detection of phase-II phenomena.

Feature Space

Figure 10:
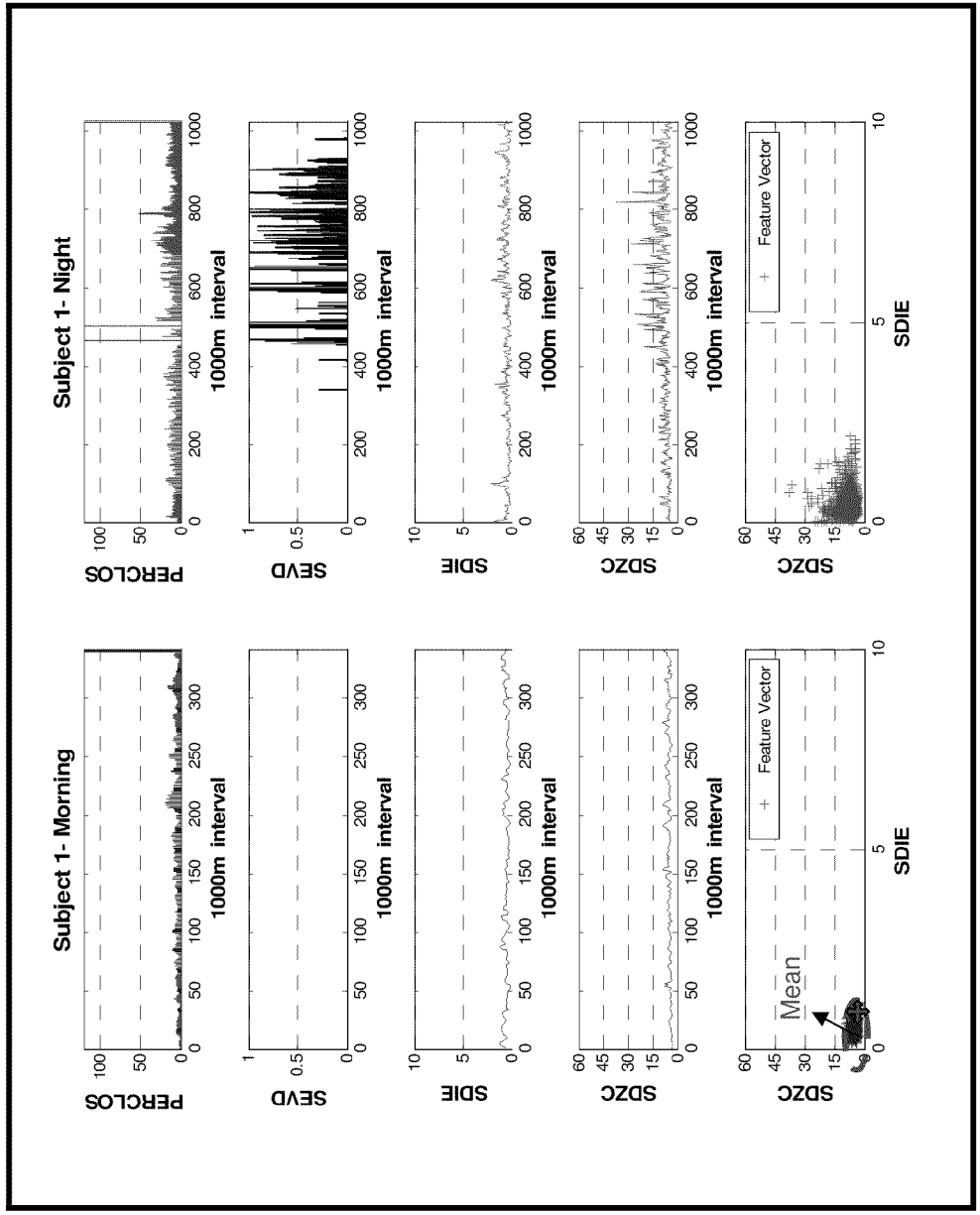
FIG. 10 is a set of graphs showing a comparison of extracted features for each driver for morning and night sessions.

Mathematically, each pair of measured features, SDIE and SDZC, can be presented together as a feature vector in a 2-dimensional feature space. Each SDIE and SDZC describes a specific phase of drowsy driving and are handled simultaneously. The feature vector is in the form of (SDIE, SDZC). Steering data collected from the truck simulation experiment were divided into smaller windows (Window size=1000 m; Stride=250 m). Values of SDIE and SDZC were calculated in each overlapping window. FIG. 10 displays values of SDIE and SDZC in each window for a sample subject during morning and night sessions as well as feature vectors for complete graphs. These values are also compared with SEVD and PERCLOS plots. The abscissa presents each 1000-m overlapping windows (intervals).

The results show increase in either SDIE trend or SDZC trend during drowsy periods (SEVD>0.5) compared to the morning sessions data. The extracted data generate clusters of alert/drowsy feature points on feature space graph. Shapes and locations of the clusters extracted from morning session data were analyzed and assessed. The analysis showed that shape and mean vector value of each cluster differed among drivers. The difference was because of each driver's unique steering control style. Some drivers prefer to control their vehicles with larger steering corrections—relatively higher SDIE—while others tend to perform less frequent steering corrections—relatively higher SDZC—during their normal driving behavior.

The steering behavior can also include both mentioned behavior. Theoretically, the shape of the cluster (alert data) can be presented as an ellipse with a long axis toward the direction of a feature that represents driver's dominant steering control behavior (See FIG. 10). That is, the bottom left plot of FIG. 10 showing SDZ vs. SDIE illustrates an elliptic shape with longer axis along the SDIE direction. The arrow in this plot represents the principal axis of this set of data points for the alert driver. Consequently each feature's range, cluster shape, and principle axes directions in normal driving status differs from driver to driver. The bottom right hand side plot of FIG. 10 shows SDZ vs. SDIE for the drowsy driving condition of the same driver. Note that how these data falls out of the boundaries of the feature (i.e. elliptic) shape of the alert driving condition.

Therefore, the system determines feature characteristics, i.e. a boundary shape of SDZC vs SDIE for a normal driving of an individual driver. The system then continuously monitors the SDZC and SDIE values during driving, and anytime a data point falls out of this boundary, it is an indication of drowsiness. This automatically accounts for both phases of drowsiness on a real-time basis. Since each feature's range, cluster shape, and principle axes directions in normal driving status differs from driver to driver, the system uses an indicator or a recording period of alert driving for each driver for the purpose of identifying these characteristics for that driver (i.e. features range, cluster shape and principal axis. This is achieved by having an alert driver push a start button to record and process data during his/her normal and alert driving. The system then records data for a pre-specified period (say 5 to 10 minutes). The system uses the recorded data to automatically calculate the aforementioned features and store it for on-line monitoring. Note the additional normalization of these features described below.

Averaging

A single measurement from a window cannot present signal behavior. Instead, more observations and measurements of the descendant neighboring/overlapping windows are required. Looking into multiple measurements, instead of a single measurement, creates a better understanding of desired behaviors that the invention captures by implementing the feature extraction module. The feature vector average value is utilized, calculated over a certain number of consecutive windows, to quantitatively model the data behavior. This process leverages the simplest statistical modeling method, averaging, and is referred as "n-point averaging".

Whitening Transform and Steering Feature Vector Normalization

The detection system has to be independent from a driver's steering control behavior and vehicle type. To this end, the detection system automatically normalizes the features based on each driver's/vehicle's steering control behavior. The normalization method of the present invention is completely automatic, and requires only sampling from the alert data. The advantage of this is that it only requires steering wheel samples of alert driving.

The mathematical solution for this challenge lies in the concept of whitening transform. The extracted feature vectors from a normal driving sample data set generally create an oval shape cluster. The cluster directions of principle axes and the mean vector are different among drivers. The present invention utilizes whitening transform to generate a generic shape for all clusters to facilitate comparison of extracted features with a generic classifier.

Figure 11:
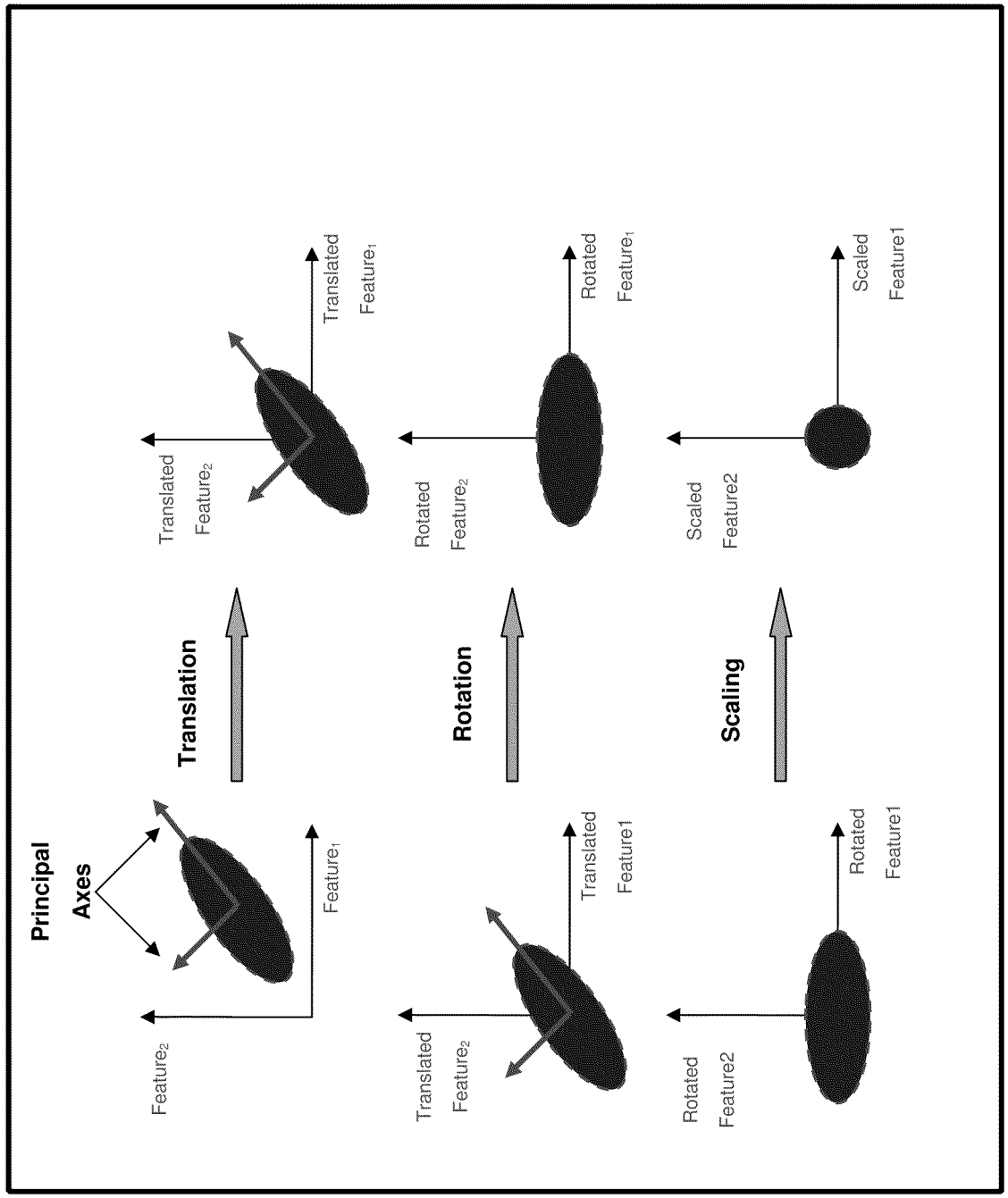
FIG. 11 are schematics of steering feature vector normalization (SFVN)

It is assumed that the introduced alert driver feature vector has a 2-dimensional elliptic normal distribution. The shape and the axes directions of the ellipse are dependent on the driver steering control behavior. In the drowsiness detection domain, the desired goal is to have a unique and generic distribution of the two independent features. This distribution can be sketched as a circle with a covariance matrix proportion to identity matrix, as shown in FIG. 11. The transformation that converts an arbitrary distribution into a circular one is called "whitening transform." Since the mean feature vector is different for each driver, before performing the whitening transform, we transfer the mean feature vector to the origin of the feature space coordinate system. The described method to normalize the steering features is so called Steering Feature Vector Normalization (SFVN).

Turning to FIG. 11, the SFVN method has three steps: translation, rotation and scaling. Translation translates the distribution mean vector to the origin of coordinate system. Based on the principle axes directions of the distribution, the coordinate system is rotated in a way that conform the principle axes. The resultant feature vectors from the previous step is then divided by each feature own standard deviation. This process produces a circular distribution with variance matrix proportional to identity matrix. The result brings the oblique oriented elliptic shape of the data cluster to a unified circular shape of unit length as shown at the end of FIG. 11, which in turn provides the ease of comparison of data that falls out of this circle during the monitoring of drivers. This all part of the feature extraction and classification modules.

Feature Extraction Procedure

The feature extractor module (as shown in FIGS. 2 and 3) carries out the following processes/calculation to provide feature vectors that can be used as classifier input: (1) SDIE and SDZC estimation for each window; (2) N-point average; and (3) Normalization using whitening transformation. The features were extracted from the data with the following specifications: Window size=1000 m, Stride=250 m, and No. of averaging points=8. To calculate the whitening transformation matrix, a sample set of randomly chosen points from the alert data points was used for each driver. The sample size was 50% of the original data size (20-30 min alert driving length). Therefore, thirteen (for 13 drivers) whitening transformation matrices were calculated where each corresponded to one subject.

Figure 12:
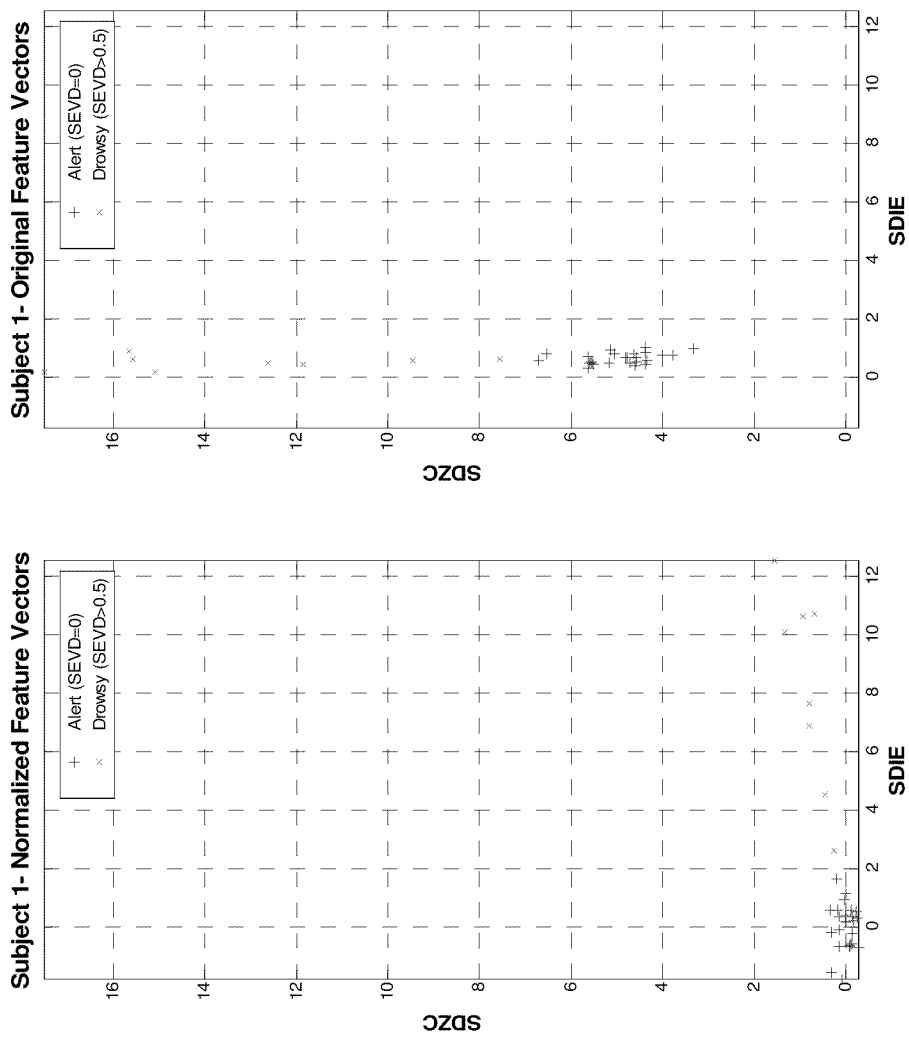
FIG. 12 is a set of graphs showing alert and drowsy feature vectors for different subjects before and after normalization.
Figure 13:
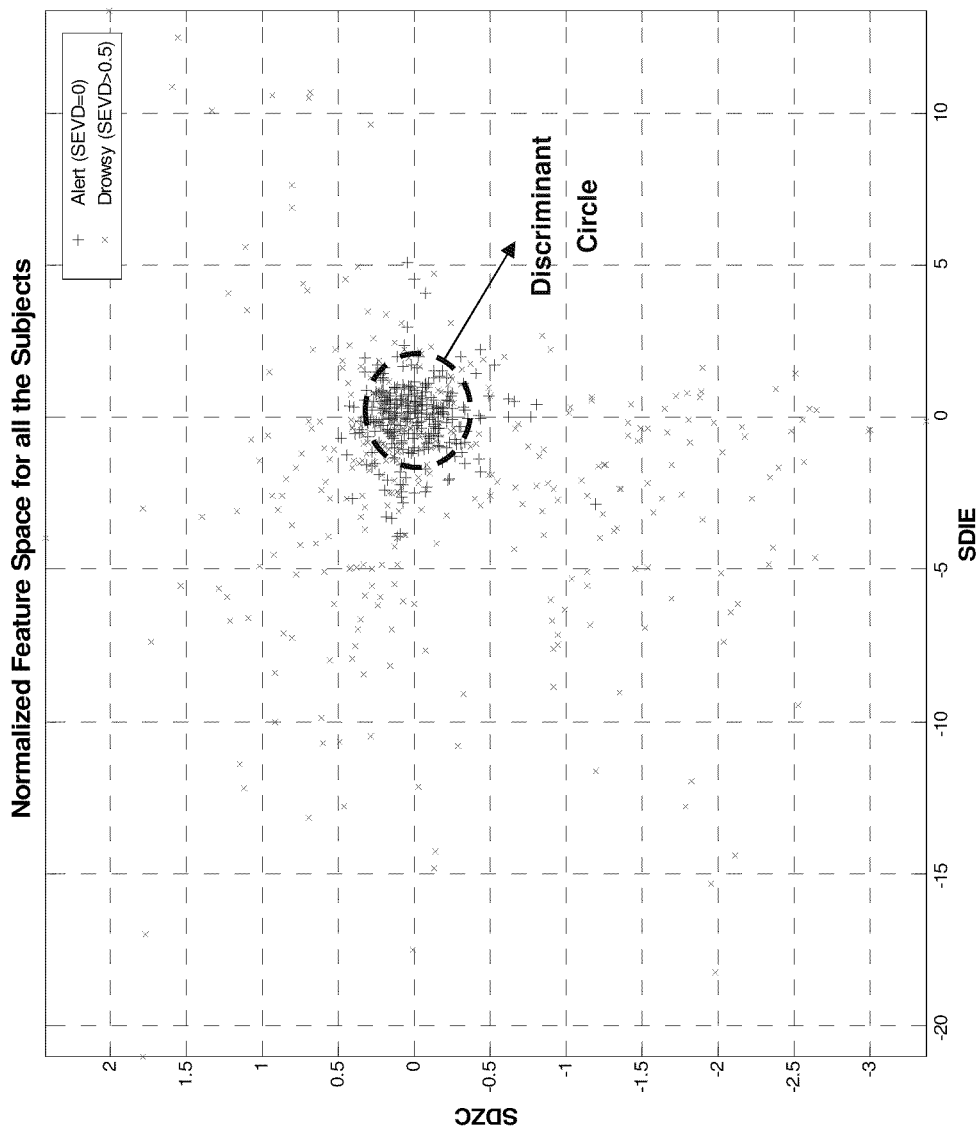
FIG. 13 is a graph showing concatenation of all feature vectors.
Figure 14A:
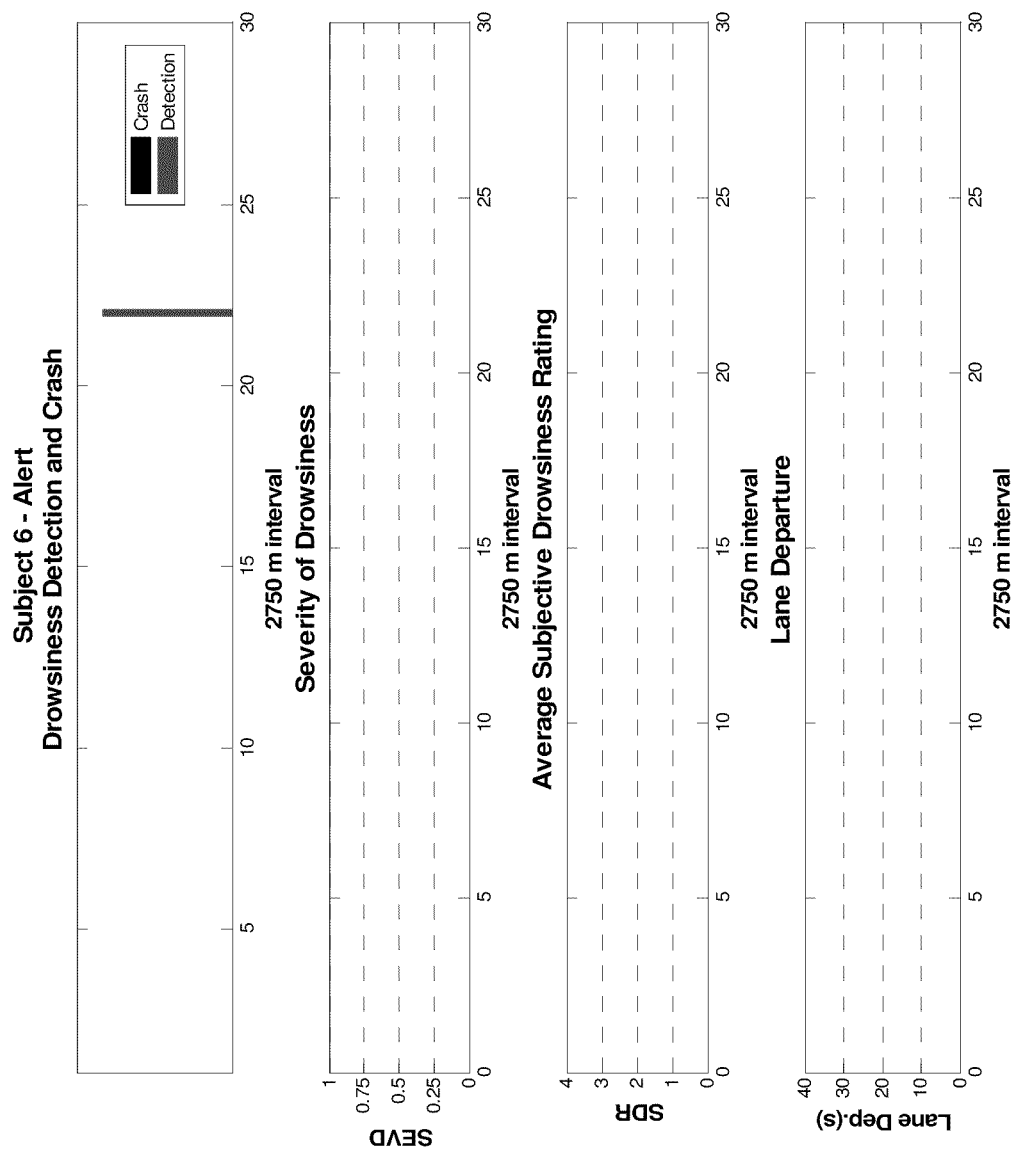
FIGS. 14(a)-(d) are graphs showing drowsiness detection algorithm results for all the subjects during morning and night sessions.
Figure 14B:
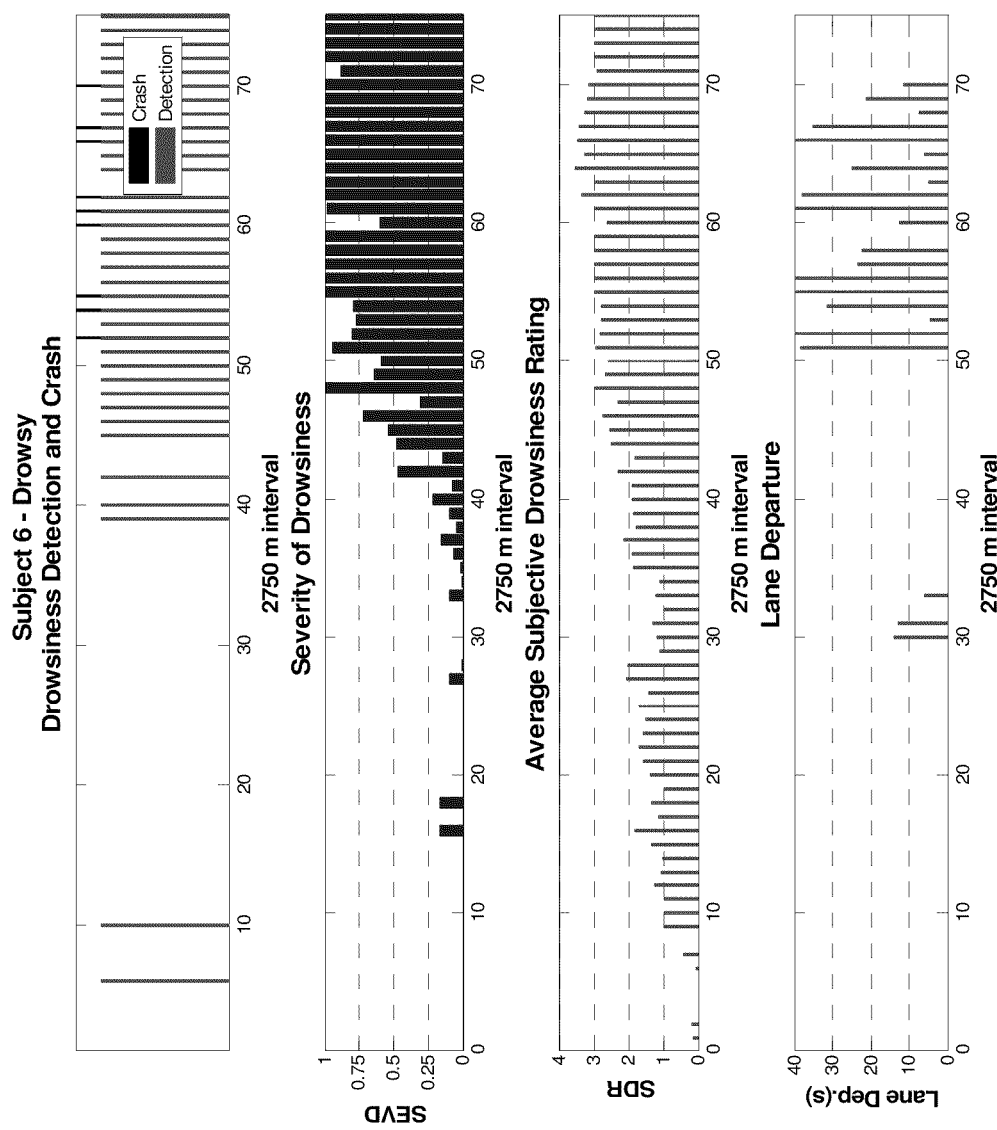
Figure 14C:
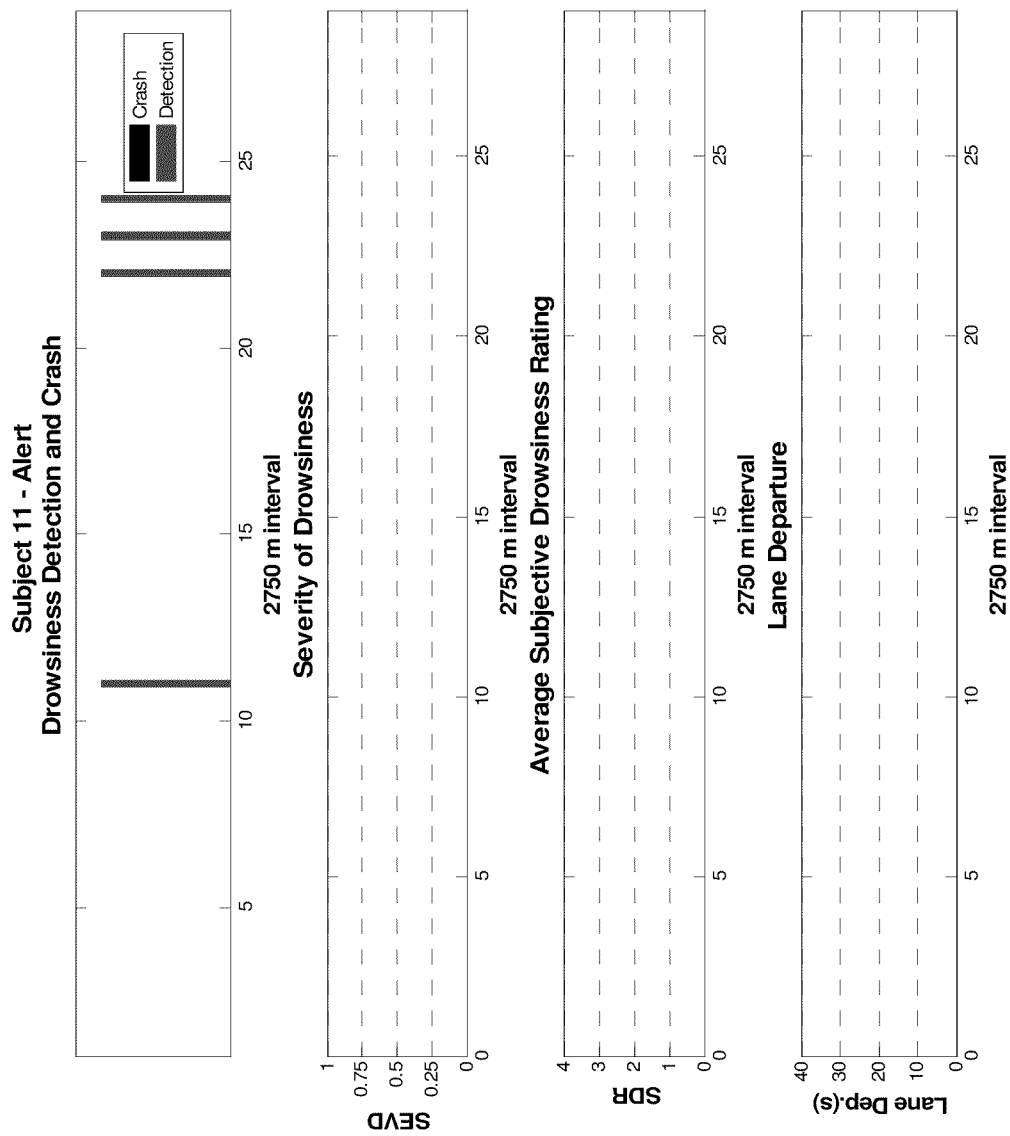
Figure 14D:
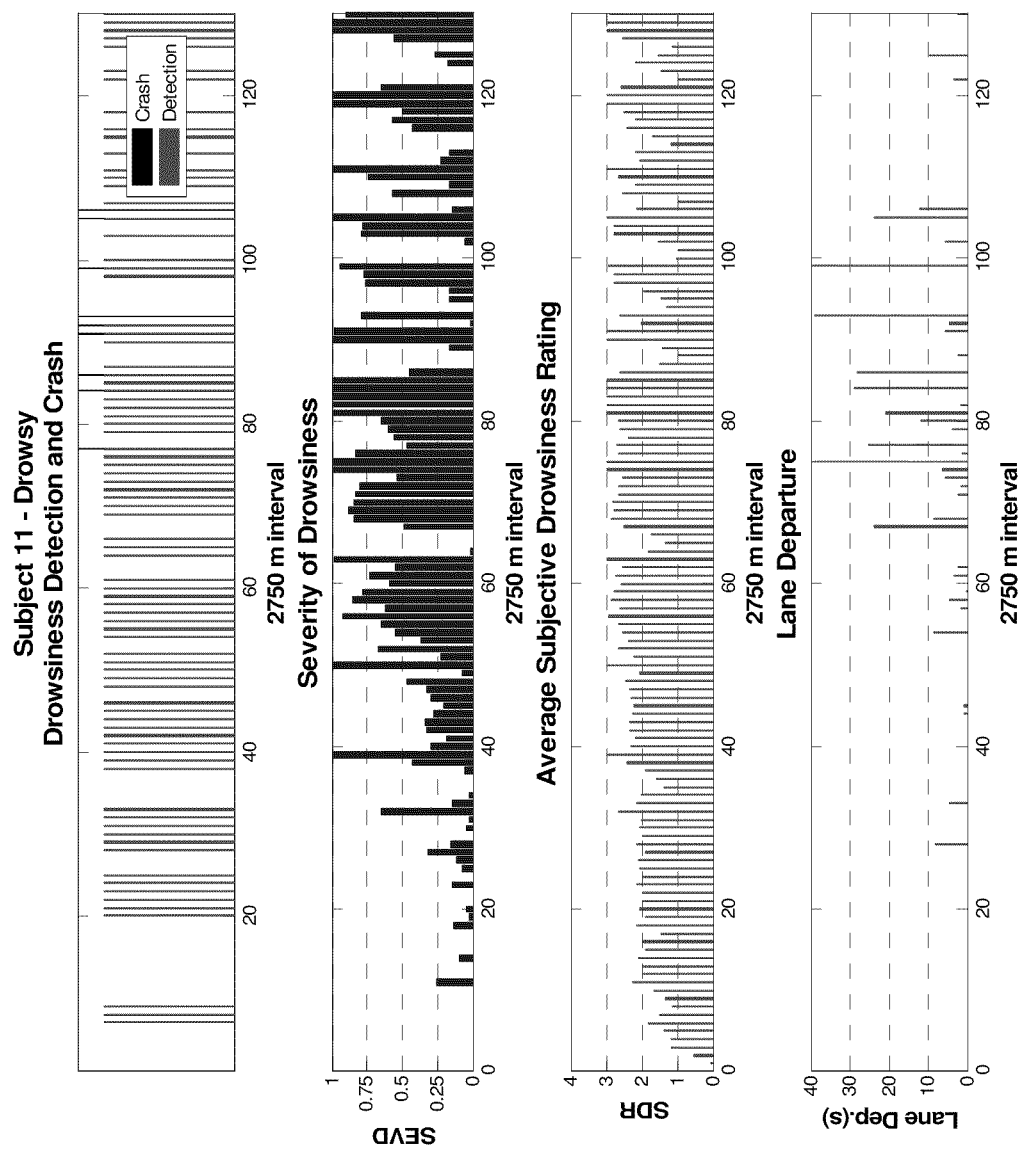

FIG. 12 displays a sample of alert (SEVD=0) and drowsy (SEVD>0.5) feature vectors (used as a training set for the classifier) of a subject before and after the normalization. Normalization helped to cluster the alert data around the center and hence provided a better discriminator between this data set and the red data set associated with drowsy driving of the same subject. FIG. 13 shows the concatenation of all the feature vectors samples after SFVN for all the drivers, and the accumulation of alert points around the origin of the coordinate system due to the normalization process. The hypothetical boundary of the normalized alert feature vectors cluster is shown as a circle, so called "discriminant circle." Ideally, the points inside the circle belong to the alert class and the points outside the circle fall into the drowsy category. However, there are few exceptions in which drowsy feature vectors are located inside the alert discriminant circle or vice versa. This is the result of the existence of occasions when the driver is drowsy, but the steering control looks normal (missed detection), or the alert driver is forced to conduct an abnormal steering control because of the traffic maneuver (false detection).

In general, as the locations of the points move radially away from the center of the circle (i.e., toward the outside of the circle), more drowsy vectors are observed.

Classification

Classifiers (as shown in FIGS. 2 and 3) aim to classify the data into different states of the nature, based on the statistical properties of the extracted features. Some methods use a set of labeled (already been classified) feature vectors (training set), which randomly selected from a pool of feature vectors, for classification. Basically, the classifier trains itself with the training set. The resulting learning scheme is referred to as "supervised" learning. Since the extracted features are normalized with respect to each driver's steering control behavior, the classifier can use any normalized training set. The labeling (i.e., when analyzing the data, the data is labeled with the degree of drowsiness with SEVD, etc., as discussed above) of the data was based on the subjective observation of the video data.

Testing and Results

The detection algorithm was tested for performance and accuracy. The accuracy of labeled data was tested by measuring different accuracy/performance parameters using labeled testing data sets. A training set was sampled randomly from a set of labeled feature vectors. In the training set, the number of alert labeled feature vectors was equal to drowsy labeled ones. The remaining of the feature vectors were used for testing. The algorithm was tested with 20 different separate random training and testing sets to obtain performance ranges. The results showed: the average accuracy, hit rate, false alarm rate and missed rate were 83%, 84%, 17% and 16% respectively. The accuracy was good, ranging from 80% to 86%.

The system was also tested for algorithm output using whole collected data. The detection system was run for each driver using a complete set of data collected during morning and night sessions and analyzed the detection system output. FIG. 14 shows the drowsiness detection outputs for two sample subjects during morning and night sessions. The abscissa represents 2750 m intervals. For each subject, there are three graphs. The first graph is output of the detection algorithm based on analyzing the steering wheel behavior of the driver. Each of the short bars (which don't quite extend to the top of the chart) shown in the top graphs of FIGS. 14(a)-(d) means the algorithm is classifying that particular interval as "drowsy" while the long bars (which extend to the top of the chart) are classified as "alert." In other words, the detection system has issued a "warning" for that interval. The second bar graph shows SEVD values over the whole session. The third bar graph displays SDR. The last graph illustrates the total time of lane departure for each interval. This parameter is referred to as the total driving time when the vehicle departed 0.5 m from the lane boundaries. This parameter is a good measurement for hazardous situations.

The system was also tested for lane departure detection. An important performance metric is the ability of the detection system accuracy to issue warnings prior to lane departure incidents. Since most of the drowsiness related crashes experienced by the subjects were because of run-off road crashes, lane departure was a good measurement for a driving hazardous situation. Warnings issued before a lane departure can be seen as legitimate warnings as opposed to false alarms. A primary purpose of the system is to prevent hazardous situations like lane departures and ultimately crashes. Thus, the most important assessment metric for a drowsiness detection system is the ability to issue a warning in a timely fashion before or during a lane departure interval.

The drowsiness detection system was analyzed for 11,000 m (4×2750 m) of driving distance, approximately 6 min driving with average speed of 65 mph, before each lane departure event. The analysis also included the lane departure event interval itself. We chose only the lane departure events with SEVD values greater than zero. The proportion of correct detection intervals to the total number of intervals, in which SEVD was greater than zero, was calculated before each lane departure event.

The purpose of the analysis was to show whether the system was capable of issuing warnings before a hazardous situation. This issue is very important since it can show that the steering degradation phases occur before lane departures and the hazardous situations are predictable. The table shown in FIG. 15 shows the system performance before lane departure events for 11,000 m/6 min before lane departures caused by drowsiness (SEVD>0). The table shows percentage of time each detections system correctly issued warnings for drowsy intervals. The existence of warnings before each lane departure event was also investigated. The study shows the system issued at least one warning before or during 97% of lane departure incidents.

It should be noted, unlike the drowsiness criteria for testing the system in which SEVD>0.5, the accuracy performance for lane departure was selected with lower threshold values (SEVD>0). This will include the intervals with moderate levels of drowsiness which indicates a significant performance for the system. Accordingly, the system can also be used (with good accuracy) with a reduced threshold to consider lower levels of drowsiness.

CONCLUSION

One objective of this invention was to develop an unobtrusive system and method of drowsiness detection system using driver's steering wheel data. The key contributions of this study include analysis of truck drivers' drowsiness behavior and development of a new drowsiness detection method that solely relies on steering wheel measurement. This system and method is robust and adaptive to drivers' different steering control behaviors. Accordingly, one major contribution of the current invention is the use of Empirical Mode Decomposition (EMD) to decompose steering wheel signals into intrinsic oscillation modes enabling the analysis of the steering signal behavior independent of the road geometry information. Having the two Phases provides more accurate results and covers larger ranges of degradation intervals.

Another major benefit of the present invention is the extraction of two features which represents the two-phase phenomenon, namely Impaired and Drowsy. This two phase identification is unique, and eliminates any need to know when there is a dangerous situation and create a countermeasure, a solution warning signals partial braking/slow down, or full control (such as engine shut down, braking, steering to safe stop).

Another major advantage of the present invention is the automatic normalization of the features for each driver based on his/her normal steering control behavior. As shown in figures, the normalization provides an easy way of characterizing the alert driving of each driver and the ease of comparison of the features during drowsy driving. This means that the system can be programmed easier, such that when a data point (i.e., a vector of the two features which are now normalized for normative alert driving) falls out of the normalized circle, it will be considered a data point associated with drowsy driving.

The present invention provides a significant correlation between drowsiness and degradation of drivers' lane keeping and steering control. Higher variability in lateral position and larger steering corrections were observed when drowsiness level was high. Standard deviation of lateral position increased, but the steering angle remained constant for periods when drivers dozed-off and stopped all steering activity. An important conclusion based on these results which complements earlier findings is that most crashes involving a drowsy driver are preceded by a two-phase phenomenon. Before a crash, large amplitude steering angle corrections start to appear and are followed by sporadic short intervals with no significant changes in steering angle reflecting the drivers' total loss of feedback control. In the present invention, SDIE picks up the large amplitude phase and SDZC picks up the constant steering angle phase, hence the invention picks up these driving characteristics/features of the drowsy driver before a crash happens.

The present invention correctly detects eighty-three percent (83%) of the drowsy intervals. The algorithm also performed with average of 84% hit rate, 17% false alarm and 16% of missed rate. The results showed a good prediction of drowsiness using the features. The present invention also showed a good performance during 11,000 meter before lane departure events. The algorithm issued at least one warning for 97% of the events and has an average of 80% detection accuracy.

Summary of the in-Vehicle Implementation of the Drowsiness Detection Algorithm

Figure 16:
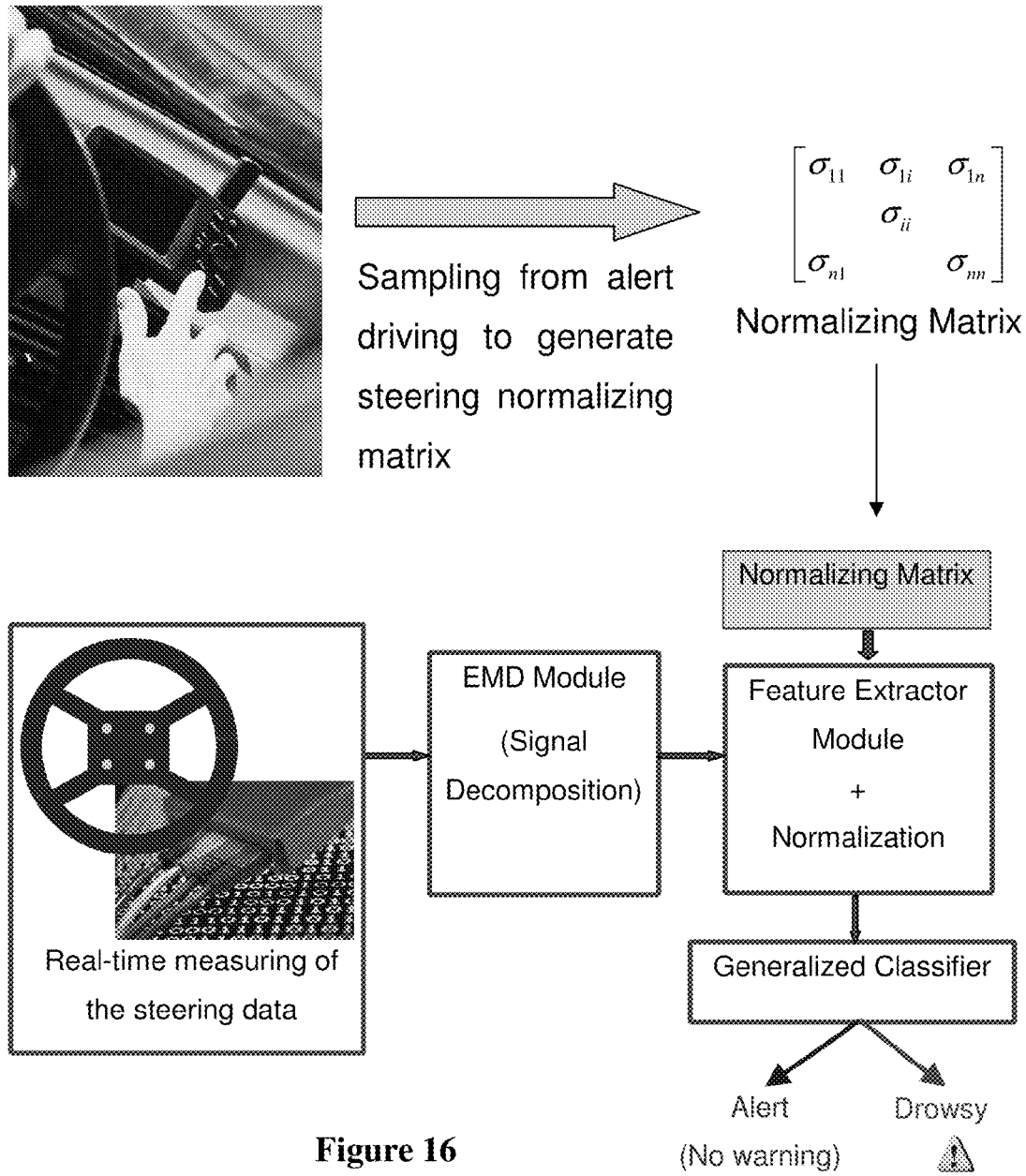
FIG. 16 is an implementation of the drowsiness detection system and method in accordance with a preferred embodiment of the invention.

FIG. 16 shows the system and method of the present invention for drowsiness detection in a vehicle. The system includes a driving wheel sensor, a processor, and an alarm device. The sensor measures the steering wheel angle, and the processor determines whether that measured angle is an indicator of drowsiness. The system is an unobtrusive method which is comfortable and does not interfere with the driver or driving activity. It does not require special expensive measurement equipment, does not monitor the driver face, or create any distraction of the driver's attention. Recording and analysis of the steering data in the algorithm is compatible and adaptable to real-time analysis of the data.

The system is preferably calibrated for each driver's steering control behavior by calculating the whitening transform matrix for that individual driver. During normal driving state, the driver can push a button to record the steering data. This provides the system enough alert data to calculate automatically the normalizing matrix. Alternatively, the system can automatically record the steering data when the vehicle is initially started, or at a predetermined period from the initial start of the vehicle, without any manual intervention. The steering data can be stored in a storage device, such as a memory or database in communication with the processor. The system then collects the steering data for a predetermined period of time, preferably longer than about 20-30 minutes. The steering data can also be stored for a period of weeks, months or years, and accessed by the driver name or other, so that it need not be repeated each time that same driver operates the vehicle.

Once the normalizing matrix is calculated, the system is calibrated for that one driver and is able to run the drowsiness detection system for that particular driver. The results show that the normalized features for normal driving are concentrated in the origin of the feature space. It is possible to extract a discriminant function (circle) which can separate the concentration of alert data from drowsy data by testing many drivers. This provides a generalized classifier which is normalized for different steering control behavior. If the future analysis of the steering data for different drivers and vehicles indicates that a unique discriminant function cannot be identified, a general classifier can be trained using various tested drivers steering data for different vehicles. This bank of data can be obtained by testing different drivers in various alertness states. The trained classifier can be programmed into the detection system, or stored in the storage device and accessed by the processor. FIG. 16 shows a schematic of the recorded steering signal being decomposed in the EMD module. The IMF-1 component is selected and the desired features are extracted from IMF1 signal. The extracted features are normalized using the calculated normalizing matrix. Then the normalized feature vector is introduced to the classifier to identify the driver state.

The method and operation of the system is implemented by a computing platform which performs the various functions and operations in accordance with the invention. The computing platform may be one or more of a wide variety of components or subsystems including, for example, a processor (as shown in the embodiments), register, data processing devices and subsystems, wired or wireless communication links, input devices, monitors, memory or storage devices such as a database. The computing platform can be contained within a vehicle, or a portion of the platform can be contained in the vehicle to wirelessly access other elements of the computing platform.

The system can utilize software, hardware or a combination of hardware and software to provide the processing functions. All or parts of the system and processes can be stored on or read from computer-readable media. The system can include computer-readable medium having stored thereon machine executable instructions for performing the processes described.

The alarm device is utilized to indicate that the driver is drowsy. When the generalized classifier determines that the driver is drowsy, the processor sends an alarm signal to the alarm device. The system can also be used with any number of suitable alarm devices to indicate that the driver is drowsy. The alarm can be, for instance, vibration of the driver and passenger seats, an audible alarm, a visual alarm, or other. The alarm can alert the driver and attempt to wake the driver, and can also alert any passengers. The alarm is activated by the system if it is determined that the driver is drowsy. It should be also be appreciated that, although the feature vector module and the classification module are shown separate from the preprocessing module in the embodiment of FIG. 2, the modules can all be implemented by software running on the processor.

The detection operation can be implemented by a separate processor, or incorporated into existing in-vehicle CPUs or computers which use the sensed steering wheel data, processes the data in real-time, and determines a drowsy (or alert) state continuously. The system is preferably implemented in a standalone device having the sensor, processor and alarm integrated therein. However, one or more of those elements can be provided in a separate device. For instance, the sensor and processor can be integrated together, but the alarm device can be tied directly to the vehicle horn, interior lights, or stereo.

Training Phase

The preferred operation of the system, as implemented for a vehicle having a steering wheel angle sensor, processor, memory device, and alarm, will now be described with reference to FIG. 3. There are two operational modes or phases of the system: a training phase and a detection phase. The training phase is to record steering wheel data while a driver is driving normally in an awake/alert situation. The objective is to come up with a personalized ground truth set, which can be used to detect steering control abnormality during the detection phase. The training phase is as follows:

1. A recording phase is initiated, either by the driver or automatically by the system. The recording takes place for about 60-km of driving.

2. The system starts recording data in separate batches real-time, i.e., as the driver is driving. The processor receives raw steering wheel angle data (such as in degrees or radians) from the sensor and records the raw data in the storage device. Each batch or window is 1,000 meters long and has an overlap with the adjacent windows every 250 meters (window strides of 250 m). The sampling frequency is 10 Hz.

3. Each recorded data window has a uniform point distribution which maintains constant 10 Hz sampling. The processor unifies the sampling by cutting extra sample points (extra data) or interpolating for missing data. The data is thus ready for further processing by the IMF algorithm.

4. Using an Empirical Mode Decomposition algorithm, the processor applies the IMF extraction process to extract IMF 1 (the first intrinsic mode) out of the steering wheel signal that is captured in the 1,000 m long window. As a result, the processor generates an IMF 1 signal as an output which is based on the corrected raw steering wheel angle data read out of the storage device.

5. The processor then calculates the absolute extrema values of the IMF 1 signal and computes the standard deviation of them, which is called Standard Deviation of IMF 1 Extreme (SDIE). This value will be used as an extracted feature from the IMF 1 signal to detect drowsiness.

6. The distances of zero-crossings of the IMF 1 (distance between two consecutive points of a signal that intercept x-axis) is calculated. The standard deviation of the resulting measurements is estimated. This value is the second extracted feature from the IMF 1 signal, called the Standard Deviation of IMF 1 Distance of Zero Crossing (SDZC), which will also be used to detect drowsiness.

7. The processor puts together the two extracted features and forms a unique pair (feature space) for each data window.

8. The measured features (SDIE and SDZC) are stored and averaged over 8 consecutive windows. The resulting pair or vector (SDIE, SDZC) is called a feature vector.

9. The processor then automatically normalizes the features (i.e. the feature vector) using the whitening transform. Normalization enables an easy form of feature identification, as described in items 10 and 11 below. The extracted feature vectors from a normal driving sample data set generally create an oval shape cluster. The cluster directions of principle axes, mean vector and shape are different among drivers. This transformation will generate a unique shape for all clusters to be compared.

The whitening transform is as follows. In the following description of the whitening transform, SDIE and SDZC are $x_1$ and $x_2$. Any general feature vector, $\vec{x}$, can be assumed as a vector of random variables, $\vec{x}(x_1, \ldots, x_n)$. $\vec{x}$ has a distribution with n-component mean vector, $\vec{\mu}$, and a n by n covariance matrix, $\Sigma$. Assuming the random variable, $\vec{x}$, has the distribution $p(\vec{x})$, mean or expectation of the vector is calculated by $$\vec{\mu} \equiv \varepsilon[\vec{x}] = \int \vec{x} p(\vec{x}) d\vec{x}$$

or $$\vec{\mu} \equiv \varepsilon[\vec{x}] = \begin{bmatrix} \varepsilon[x_1] \\ \varepsilon[x_2] \\ \vdots \\ \varepsilon[x_n] \end{bmatrix} = \begin{bmatrix} \mu_1 \\ \mu_2 \\ \vdots \\ \mu_n \end{bmatrix}$$

The covariance matrix is defined $$\underline{\Sigma} = \varepsilon[(\vec{x} - \vec{\mu})(\vec{x} - \vec{\mu})^t] = \int (\vec{x} - \vec{\mu})(\vec{x} - \vec{\mu})^t p(\vec{x}) d\vec{x}$$

where $$\underline{\Sigma} = \begin{bmatrix} \sigma_{11} & \sigma_{12} & \ldots & \sigma_{1n} \\ \sigma_{21} & \sigma_{22} & \ldots & \sigma_{2n} \\ \vdots & \vdots & \vdots & \vdots \\ \sigma_{n1} & \sigma_{n2} & \ldots & \sigma_{nn} \end{bmatrix}$$

The diagonal elements of $\Sigma$, $\sigma_{ii}$, are the variances of $x_i$'s and the off-diagonal elements, $\sigma_{ij}(i \neq j)$, are covariances of the elements $x_i$ and $x_j$. The components of the feature vector ($x_i$ and $x_j$) are independent when $\sigma_{ij}=0$, for $i \neq j$. If the principle axes of $\Sigma$ are not parallel to the feature space axes, the features are dependent.

Since the mean feature vector was different for each driver, before performing the whitening transform, the mean feature vector is transferred to the origin of the coordinate system. Therefore the new feature vectors are $\vec{x}'_i = \vec{x}_i - \vec{\mu}$, where $\vec{x}_i$ is the original feature vector and $\vec{\mu}$ is the mean feature vector. If we define $\Phi$ to be the matrix whose columns are the orthonormal eigenvectors of $\Sigma$ (covariance matrix of new feature vectors), and $\Lambda$ to be the diagonal matrix of the corresponding eigenvalues, the whitening transform $A_w = \Phi \Lambda^{-1/2}$ can be applied to the coordinates of the original distribution (i.e. the features of SDIE and SDZC.) The transformed distribution has a covariance matrix proportion to identity matrix. For our problem, $\Phi$ and $\Lambda$ matrices are 2 by 2. The described method to normalize the steering features is called steering feature vector normalization (SFVN). The system calculates and stores the 2×2 $A_w$, to be applied on extracted features during the detection phase.

10. The processor puts the calculated feature vectors during the training phase together and generates a feature space that looks like a circular cluster centered at (0,0). The boundaries of the cluster forms a discriminant circle.

11. The equation of the discriminant circle (the cluster boundary) can be defined by using the transformed and stored data.

At this point, the processor stores the normal feature vector and the radius for the circular cluster in the storage device. Other data, such as the raw steering wheel data, is not needed for the detection phase, though could be optionally be stored.

Detection Phase

The training phase automatically ends when sufficient data has been recorded in the memory device. The processor then automatically switches to the detection phase. In this phase, the system is operational and ready to detect driver awareness. The detection phase is as follows:

1. The processor starts recording data in separate batches real-time and storing the data in the storage device. Each batch or window is the same as during the training phase, namely 1,000 meter long and has overlap with the adjacent windows every 250 meters (window strides of 250 m), and a sampling frequency of 10 Hz.

2. Each recorded data window has to have a uniform point distribution in which maintains constant 10 Hz sampling. The system unifies the sampling by cutting extra sample points or interpolating the missing data.

3. Using the Empirical Mode Decomposition algorithm, the processor applies the IMF extraction process to extract IMF 1 (the first intrinsic mode) out of the steering wheel signal that is captured in the 1,000 m long window.

4. The processor then calculates the absolute extrema values of IMF 1 signal and computes the standard deviation of them, which is called Standard Deviation of IMF 1 Extreme (SDIE). This value will be used as an extracted feature to detect drowsiness.

5. The distances of zero-crossings of the IMF 1 (distance between two consecutive points of a signal that intercept x-axis) is calculated. The standard deviation of the resulting measurements is estimated. This value is the second extracted feature, so-called Standard Deviation of IMF 1 Distance of Zero Crossing (SDZC), which will also be used to detect drowsiness.

6. The processor puts together the two extracted features and forms a unique pair (feature space) for each data window.

7. The measured features (SDIE and SDZC) are stored in the storage device and averaged over 8 consecutive windows.

8. The system multiplies this vector by the 2×2 $A_w$, matrix stored in the memory during training phase. The result is a 1×2 vector.

9. Accordingly, steps 1-8 of the detection phase are essentially the same as steps 2-10 of the training phase. At this point, the system compares the normal feature vector and the radius for the circular cluster stored in the storage device from the training phase with the vector from step 8 of the detection phase. Any points which fall within the discriminant circle boundary (found on step 11 of the training phase) is defined awake and any feature vector outside the boundary is classified as drowsy. This step corresponds to the classification module shown in FIG. 3.

10. If a drowsy detection is made, the processor sends an alarm signal to the alarm device, which is thereby activated to awaken the driver. The alarm can be an auditory, visual, or haptic alert, or other suitable alarm device. Optionally, the system can include a mechanism which brings the vehicle to a stop or takes other safety preventative measures.

The foregoing description and drawings should be considered as illustrative only of the principles of the invention. Numerous applications of the invention will readily occur to those skilled in the art. Therefore, it is not desired to limit the invention to the specific examples disclosed or the exact construction and operation shown and described. Rather, all suitable modifications and equivalents may be resorted to, falling within the scope of the invention.

We claim:

1. A system for determining whether a driver of a vehicle is drowsy, the system comprising:
    steering wheel sensor configured to generate a steering wheel signal;
    a processor configured to extract at least one feature of the steering wheel signal by identifying a pair of consecutive zero-crossings where the signal values are zero, determine a distance between the pair of consecutive zero-crossings, repeat the identifying and distance determining steps for a plurality of pairs of consecutive zero-crossings, determine a standard deviation of the distances, determine whether the driver is drowsy based on the standard deviation, and generate an alarm signal in response to determining that the driver is drowsy, wherein the processor is more likely to determine that the driver is drowsy as the standard deviation increases relative to a normal standard deviation for the driver; and,
    an alarm device configured to indicate that the driver is drowsy, or a safety mechanism for controlling the vehicle, wherein the alarm device or safety mechanism receives the alarm signal from said processor and is activated in response to the alarm signal.

2. The system of claim 1, wherein the steering wheel signal includes an angle of the steering wheel.

3. The system of claim 1, wherein the at least one extracted feature is independent of road curvature.

4. The system of claim 1, wherein the at least one extracted feature is representative of steering control degradation phases.

5. The system of claim 1, wherein the steering wheel signal includes a lane keeping waveform.

6. The system of claim 1, wherein the steering wheel signal includes a curve negotiation waveform.

7. The system of claim 1, wherein the at least one extracted feature comprises two features.

8. The system of claim 1, wherein the processor further automatically normalizes the at least one extracted feature based on a normal steering control behavior of the driver.

9. The system of claim 1, wherein the processor records a normal steering control behavior of the driver.

10. The system of claim 9, further comprising a manually-operated switch for activating the processor to record the normal steering control behavior of the driver.

11. The system of claim 1, wherein the processor generates the alarm signal if it is determined that the driver is drowsy.

12. The system of claim 1, wherein the determining is independent of road geometry.

13. The system of claim 1, wherein the determining automatically compensates between drivers.

14. The system of claim 1, wherein the processor uses empirical mode decomposition to decompose steering wheel signals into intrinsic oscillation modes enabling the analysis of the steering signal behavior independent of road geometry.

15. The system of claim 1, wherein if said processor detects a large amplitude steering angle correction followed by sporadic short intervals with no significant changes in steering angle, said processor determines that the driver is drowsy.

16. A system for determining whether a driver of a vehicle is drowsy, the system comprising:
    a steering wheel sensor for generating a steering wheel angle signal;
    a processor configured to window the steering wheel signal by dividing the steering wheel signal into a plurality of consecutive sequences of data frames, each data frame having steering wheel data that overlaps with an adjacent data frame;
    said processor further configured to decompose the windowed steering wheel data based on an empirical mode decomposition intrinsic mode function 1;
    said processor further configured to determine whether the driver is drowsy based on said decomposed steering wheel data, and generating an alarm signal; and
    an alarm device for indicating that the driver is drowsy, or a safety mechanism for controlling the vehicle, wherein the alarm device or safety mechanism receives the alarm signal from said processor and is activated in response to the alarm signal.

17. The system of claim 16, said processor further configured to extract a first feature and a second feature of the windowed steering wheel signal, wherein the first feature is a standard deviation of extrema of the empirical mode decomposition intrinsic mode function 1, and said second feature is a standard deviation of a distance between two consecutive zero crossings of the empirical mode decomposition intrinsic mode function 1, wherein the processor is more likely to determine that the driver is drowsy as the standard deviation increases relative to a normal standard deviation for the driver.

18. The system of claim 17, wherein the at least one extracted feature is representative of steering control degradation phases.

19. The system of claim 18, wherein the steering control degradation phases include drowsy and impaired.

20. The system of claim 1, said processor further configured to window the steering wheel signal by dividing the steering wheel signal into a plurality of consecutive sequences of data frames, each data frame having steering wheel data that overlaps with an adjacent data frame.

21. The system of claim 20, wherein said processor determines the standard deviation of the zero-crossings for each of the plurality of data frames, and wherein said processor determines whether the driver is drowsy based on the standard deviation of the distances between two consecutive zero-crossings for all of the plurality of data frames.

22. The system of claim 1, said processor further configured to identify a maximum extrema value and a minimum extrema value in the windowed steering wheel signal, and determine a standard deviation of the zero-crossings and a standard deviation of the maximum and minimum extrema values, wherein said processor determines whether the driver is drowsy based on the standard deviation of the zero-crossings and the standard deviation of the maximum and minimum extrema values.

23. A system for determining whether a driver of a vehicle is drowsy, the system comprising:
a steering wheel sensor configured to generate a steering wheel signal;
a processor configured to window the steering wheel signal by dividing the steering wheel signal into a plurality of consecutive sequences of data frames, each data frame having steering wheel data that overlaps with adjacent data frames, said processor further configured to identify a maximum extrema value and a minimum extrema value in the windowed steering wheel signal, determine a standard deviation for the maximum and minimum extrema values, determine whether the driver is drowsy based on the standard deviation, and generate an alarm signal in response to determining that the driver is drowsy, wherein the processor is more likely to determine that the driver is drowsy as the standard deviation increases relative to a normal standard deviation for the driver; and,
an alarm device configured to indicate that the driver is drowsy, or a safety mechanism for controlling the vehicle, wherein the alarm device or safety mechanism receives the alarm signal from said processor and is activated in response to the alarm signal.

* * * * *